(12) United States Patent
Bowman et al.

(10) Patent No.: US 10,709,466 B2
(45) Date of Patent: Jul. 14, 2020

(54) OBSTRUCTION REMOVAL SYSTEM

(71) Applicant: MicroVention, Inc., Aliso Viejo, CA (US)

(72) Inventors: Heath Bowman, Trabuco Canyon, CA (US); Jared Shimizu, Irvine, CA (US); Kiet Lam, Moreno Valley, CA (US); Jeff Inlow, Capistrano Beach, CA (US)

(73) Assignee: MicroVention, Inc., Aliso Viejo, CA (US)

(*) Notice: Subject to any disclaimer, the term of this patent is extended or adjusted under 35 U.S.C. 154(b) by 155 days.

(21) Appl. No.: 15/821,409

(22) Filed: Nov. 22, 2017

(65) Prior Publication Data

US 2018/0140315 A1    May 24, 2018

Related U.S. Application Data

(60) Provisional application No. 62/426,113, filed on Nov. 23, 2016.

(51) Int. Cl.
*A61B 17/221* (2006.01)
*A61B 17/22* (2006.01)
*A61B 17/3207* (2006.01)
*A61B 90/00* (2016.01)

(52) U.S. Cl.
CPC ...... *A61B 17/221* (2013.01); *A61B 17/22031* (2013.01); *A61B 17/3207* (2013.01); *A61B 17/320725* (2013.01); *A61B 2017/2212* (2013.01); *A61B 2017/22034* (2013.01); *A61B 2090/3966* (2016.02)

(58) Field of Classification Search
CPC .... A61F 2/01; A61F 2002/016; A61B 17/221; A61B 17/22031; A61B 17/3207; A61B 17/320725; A61B 2017/22034; A61B 2017/2212
See application file for complete search history.

(56) References Cited

U.S. PATENT DOCUMENTS

| | | |
|---|---|---|
| 6,254,571 B1 | 7/2001 | Hart |
| 6,660,021 B1 | 12/2003 | Palmer et al. |
| 6,702,834 B1 | 3/2004 | Boylan et al. |
| 7,044,134 B2 | 5/2006 | Khairkhahan et al. |
| 9,211,132 B2 | 12/2015 | Bowman |
| 2002/0002383 A1 | 1/2002 | Sepetka et al. |
| 2003/0120303 A1 | 6/2003 | Boyle et al. |
| 2005/0192620 A1 | 9/2005 | Cully et al. |
| 2005/0228417 A1 | 10/2005 | Teitelbaum et al. |
| 2006/0264974 A1 | 11/2006 | Khachin et al. |
| 2008/0119889 A1 | 5/2008 | Kusleika |
| 2008/0234722 A1 | 9/2008 | Bonnette et al. |
| 2008/0275488 A1 | 11/2008 | Fleming |
| 2009/0299403 A1 | 12/2009 | Chanduszko et al. |
| 2010/0137892 A1 | 6/2010 | Krolik et al. |

(Continued)

OTHER PUBLICATIONS

WIPO, U.S. International Search Authority, International Search Report and Written Opinion dated Oct. 16, 2013 in International Patent Application No. PCT/US2013/048322, 12 pages.

*Primary Examiner* — Ashley L Fishback
(74) *Attorney, Agent, or Firm* — Inskeep IP Group, Inc.

(57) ABSTRACT

An obstruction removal device is described, having one or more engaging members which can engage portions of the clot. The one or more engaging members have a collapsed, delivery state, and an expanded, deployed state.

14 Claims, 21 Drawing Sheets

(56) References Cited

U.S. PATENT DOCUMENTS

| | | |
|---|---|---|
| 2011/0082493 A1 | 4/2011 | Samson et al. |
| 2011/0125181 A1 | 5/2011 | Brady et al. |
| 2011/0213403 A1 | 9/2011 | Aboytes |
| 2013/0245745 A1 | 9/2013 | Vong et al. |
| 2013/0345739 A1* | 12/2013 | Brady .................. A61B 17/221 606/200 |
| 2014/0288588 A1 | 9/2014 | Lam et al. |
| 2016/0058459 A1 | 3/2016 | Bowman et al. |
| 2017/0071614 A1* | 3/2017 | Vale .................... A61B 17/221 |

* cited by examiner

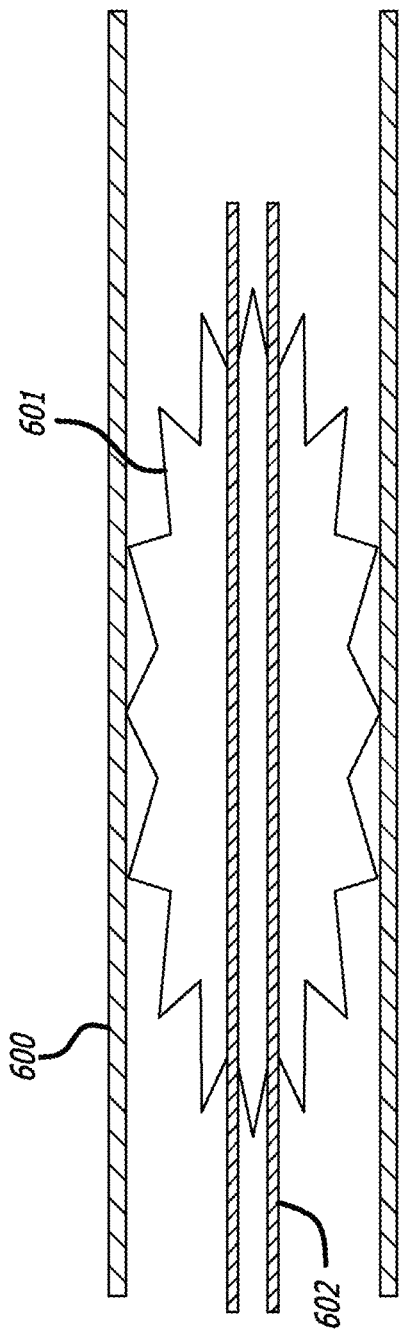
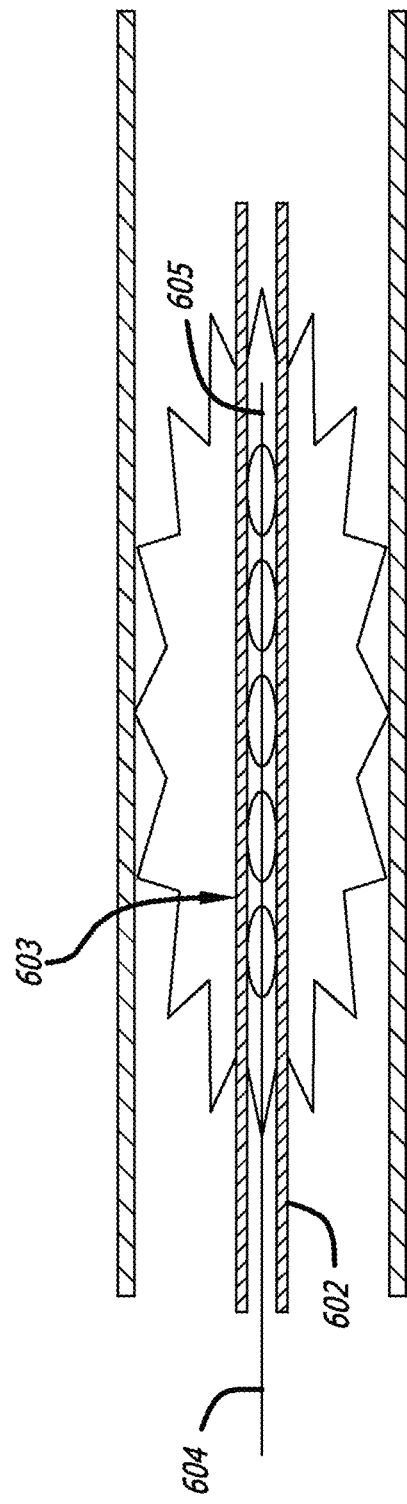

OBSTRUCTION REMOVAL SYSTEM

RELATED APPLICATIONS

This application claims priority to U.S. Provisional Application Ser. No. 62/426,113 filed Nov. 23, 2016 entitled Obstruction Removal System, which is hereby incorporated herein by reference in its entirety.

BACKGROUND OF THE INVENTION

The present invention relates to devices used to capture and remove obstructions, such as clots or other matter, from the vascular system, and delivery of these devices to a target area within the vascular system.

The buildup of thrombi in vasculature can lead to formation of blood clots. The formation of clots can result in restricted blood supply to downstream areas of the vasculature. When located in the neurovascular system, these clots can lead to stroke.

Recent technologies to remove clots utilize devices designed to hold and capture the clot, followed by withdrawal of the device to physically remove the captured clots from the body. Several of these devices may fail to capture the clot in its entirety, or may promote clot fragmentation which may allow thrombi to dislodge and accumulate at another site, thus continuing the risk of stroke. In addition, several of these devices may promote endothelial denudation due to high friction between the device and the vessel wall.

There is need for an obstruction removal device which reduces the likelihood of fragmented thrombi staying in the vasculature while maximizing the chance of mechanically capturing the clot, and limiting the risk of endothelial denudation.

SUMMARY OF THE INVENTION

In one embodiment according to the present invention, an obstruction removal device is described having a proximal axial core structure, a distal bumper structure and one or more engaging members mounted to the distal bumper structure.

In another embodiment according to the present invention, an obstruction removal device is described having a proximal structure, distal structure, and one or more connected engaging members between the two structures.

In another embodiment according to the present invention, an obstruction removal device is described having a proximal structure, distal structure, and one or more connected engaging members between the two structures, where at least one of the engaging members acts as a filter.

In one example of the previously described embodiments, the plural engaging members are substantially similar to each other.

In another example of the previously described embodiments, some of the plural engaging members are not substantially similar to the other engaging members.

In another example of the previously described embodiments, some of the plural engaging members actively engage the clot while one or more of the remaining engaging members do not engage the clot.

In one embodiment, the obstruction removal device is sheathed within a delivery device and delivered through a catheter.

In another embodiment, the obstruction removal device is delivered directly through the catheter.

In another embodiment, the device is used to retrieve foreign objects.

In one embodiment, the obstruction removal device comprises a plurality of obstruction engaging members linked together with individual linkages. The linkages link a pair of engaging members together.

In one embodiment, the obstruction removal device comprises one or more engaging members where the engaging members include some struts spanning the entire length of the elements and some struts that do not span the entire length of the elements. Some of these struts have radiopaque markers to augment imaging of the obstruction removal device.

In one embodiment, the obstruction removal device comprises one or more engaging members where the engaging members include twisted struts. The twisted struts provide a non-parallel surface which contacts the blood vessel wall, better enabling the twisted struts to scrape the vessel walls and remove hard or calcified clot.

In one embodiment, the obstruction removal device comprises one or more catch elements and one or more engaging members which engage the clot. In one embodiment, the catch elements and engaging members sit on a common core wire. In one embodiment, the catch elements can slide on or over the core wire while the engaging members are fixed to the core wire.

In one embodiment, the obstruction removal device comprises a plurality of fixed non-rotating engaging members which are rotatably offset from each other a certain number of degrees.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 10-12 illustrate a method of deploying the obstruction removal device described in the previous embodiments.

DESCRIPTION OF EMBODIMENTS

Figure 1:
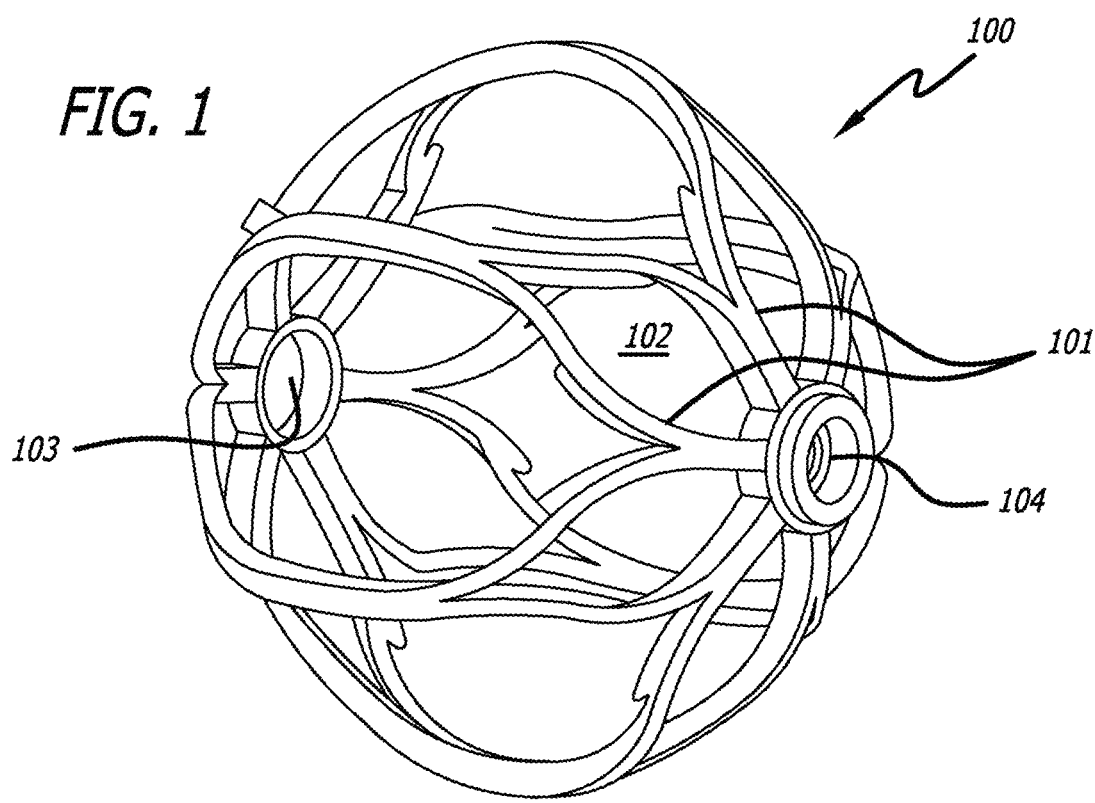
FIG. 1 is an engaging member used in an obstruction removal device.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in, the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For the purposes of the terminology described below, the terms clot, thrombus, embolus, and obstruction can be used synonymously. Though an obstruction removal device is described, the device can also be used to capture clots, thrombi, emboli, foreign bodies, or other matter. Engaging members on the device can engage clot, thrombus, embolus, foreign bodies, obstructions, or other matter.

Figure 2:
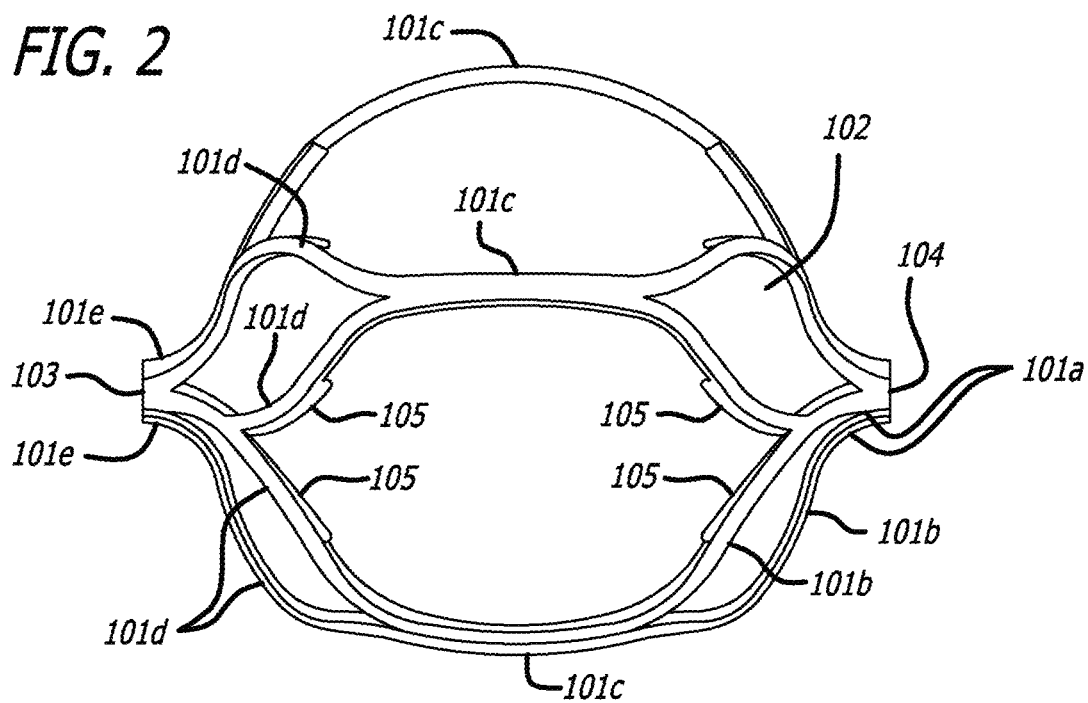
FIG. 2 is another view of the engaging member used in an obstruction removal device.

FIGS. 1 and 2 show an engaging member 100 used with the obstruction removal device of the present invention. One or more engaging members are used as part of an obstruction removal device in order to engage thrombus which can accumulate within a vascular system. General engaging member shapes can include, but are not limited to, round, oval, elliptical, hourglass, spherical, basket, stent, countered, rectangular, prismatic, cage. Each engaging member 100 has a number of struts 101 which define a number of cells, or openings 102, and a pair of opposing holes 103 and 104. For the sake of convention, hole 103 is a distal hole and hole 104 is a proximal hole.

Each engaging member may be uniquely configured with different struts, cells, cell sizes, materials, and/or shapes. The strut design can have a linear, wave, sinusoidal, or zig-zag pattern, or can have a non-symmetrical design (i.e. where struts on one side of the engaging member are not mirrored on the other side of said engaging member). The non-symmetrical strut design may help facilitate a rotational component on the member as it travels through a vessel, by shifting the center of gravity from the geometric center of the engaging member. This ease of rotation makes it easier for the engaging members, and therefore the obstruction removal device, to move more easily through the anatomy, especially after the clot has been engaged and the device is being pulled back through the vasculature. This ease of rotation can also limit the amount of damage to the vessel wall due to excessive contact friction by limiting the damage to a particular section of the wall. The engaging members may have either identical or unique designs on each end of the engaging member. This may be done by varying shape of the struts and/or cells, and/or varying the cell density of each end, thus—for example—allowing for large cell sizes on one end and smaller cell sizes on the opposing end. This variability may allow for different properties to allow for enhanced ability to engage the clot, or enhanced ability to track the obstruction removal device and deployed engaging members through the vessel.

FIG. 2 shows an engaging member 100 having a plurality of struts 101 having different thicknesses. More specifically, a plurality of end struts 101a branch out from the material defining proximal hole 104, and one or more of these struts 101a split to form struts 101b. Struts 101b are shown with features 105 protruding therefrom. Features 105 may be any interruption in the otherwise continuous surface of the strut 101. Non-limiting examples include barbs, bumps, protrusions, spikes, branches, nubs, and the like. The struts 101b are then shown as joining an adjacent struts 101b to form thicker struts 101c, which then split again to form additional struts 101d, also shown as having features 105. These struts 101d then join together again to form thicker struts 101e, which are connected to define distal hole 103. As such, it is seen that, in this particular embodiment, the struts interconnect to form a web of struts that span from the proximal hole 104 to the distal hole 103.

Another strut configuration could utilize a single strut pattern. An example includes a contiguous, helical strut configuration running between the proximal and distal ends of the engaging member, or running between a portion of the length spanning the proximal and distal ends of the engaging member.

Each engaging member has a collapsed configuration when sheathed within a delivery device, and takes on an expanded configuration as shown in FIGS. 1 and 2 when unsheathed. Each engaging member can be self-collapsible and self-expandable based on whether an external force is applied to constrain it (as would be the case when sheathed in a delivery device), or no constraining force is present (as would be the case when unsheathed).

The engaging member may be formed from nitinol, or a similar material, and may be laser cut to achieve the profile shape. Other materials and other cutting and/or machining processes would fit within the scope of the invention.

The distal and proximal holes, 103 and 104, on respective distal and proximal end of the engaging member, may facilitate placement of a common rod on which each engaging member sits, or they may fit separate connection pieces to connect multiple components of the obstruction removal device with the respective engaging members.

Figure 3:
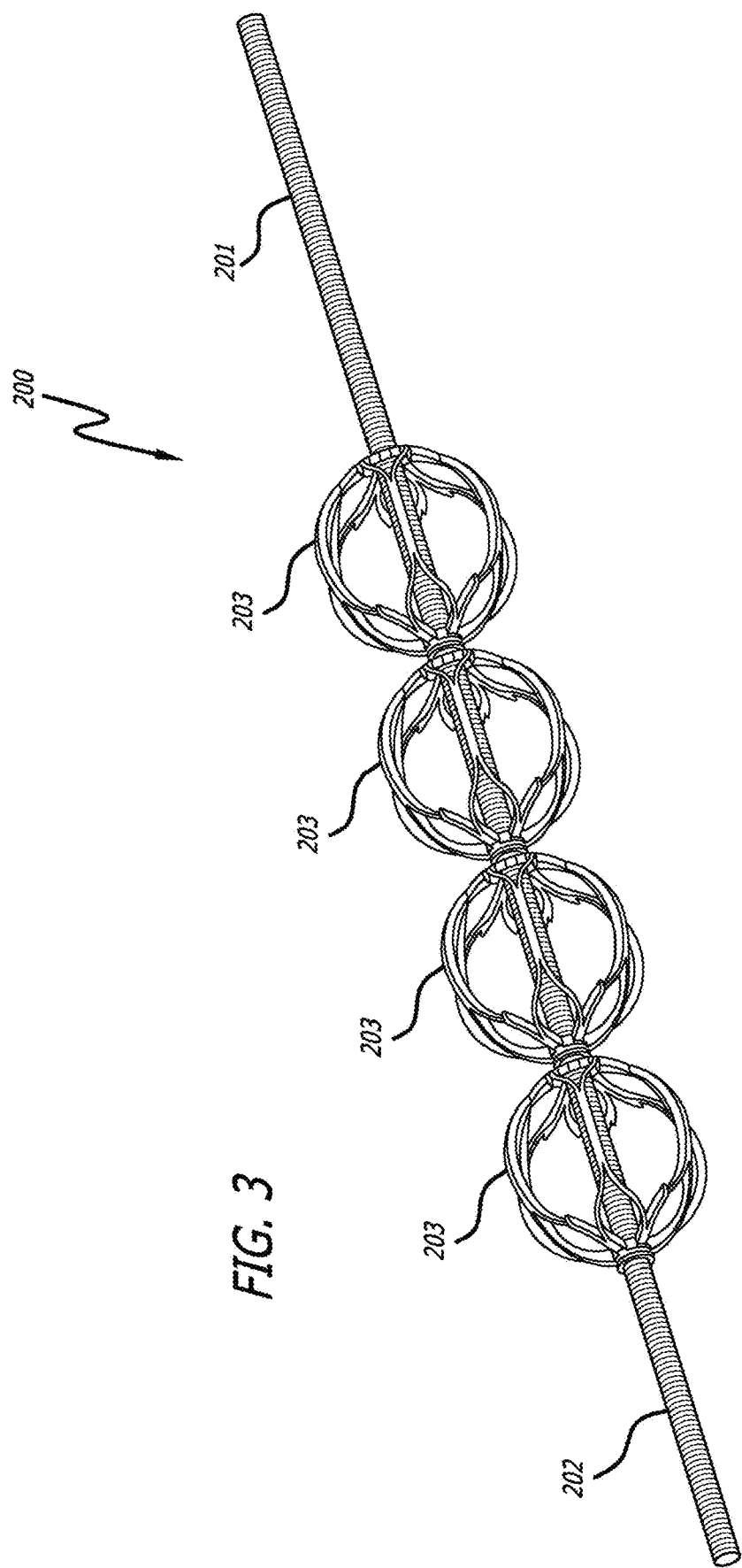
FIG. 3 is an obstruction removal device according to one embodiment of the present invention.

FIG. 3 illustrates an obstruction removal device 200 according to one embodiment of the present invention. The obstruction removal device comprises a proximal core structure 201 at one end of the device, a distal bumper structure 202 connected to the proximal core structure 201, and one or more engaging members 203 mounted to the distal bumper structure 202. In one example, the device is pushed and/or pulled from the core structure 201 end. A pusher may sit under the core structure, or the core structure itself may act as a pusher.

Core structure 201 may be made of a variety of materials, including, but not limited to, nitinol, stainless steel, cobalt chromium, or a polymeric material such as PTFE, Pebax, TPE, Engage, polyethylene, or other similar materials. Core structure configurations can include, but are not limited to, a coil, a braid, or a coil/braid combination.

The bumper structure 202 may be made of a radiopaque material, including, but not limited to, platinum, tantalum, palladium, or other similar material. A radiopaque material is preferred to make imaging of the device easier during the device insertion procedure, although non-radiopaque materials may also be used. The engaging members being mounted to the bumper structure, where the bumper structure is made of a radiopaque material, aids in imaging the device during the clot removal procedure. The engaging members may be mounted to the bumper structure in several ways. For example, the bumper structure may have a threaded outer profile, where the holes of the engaging members have a corresponding receiving structure to rotatably mate to the threaded bumper structure profile. Alternatively, the bumper structure may have a non-threaded outer configuration, and the engaging members may be affixed to the bumper structure by a heat treatment procedure, such as welding. Other mechanical means or other heat treatment procedures can also be used to affix the engaging members to bumper structure.

Figure 4:
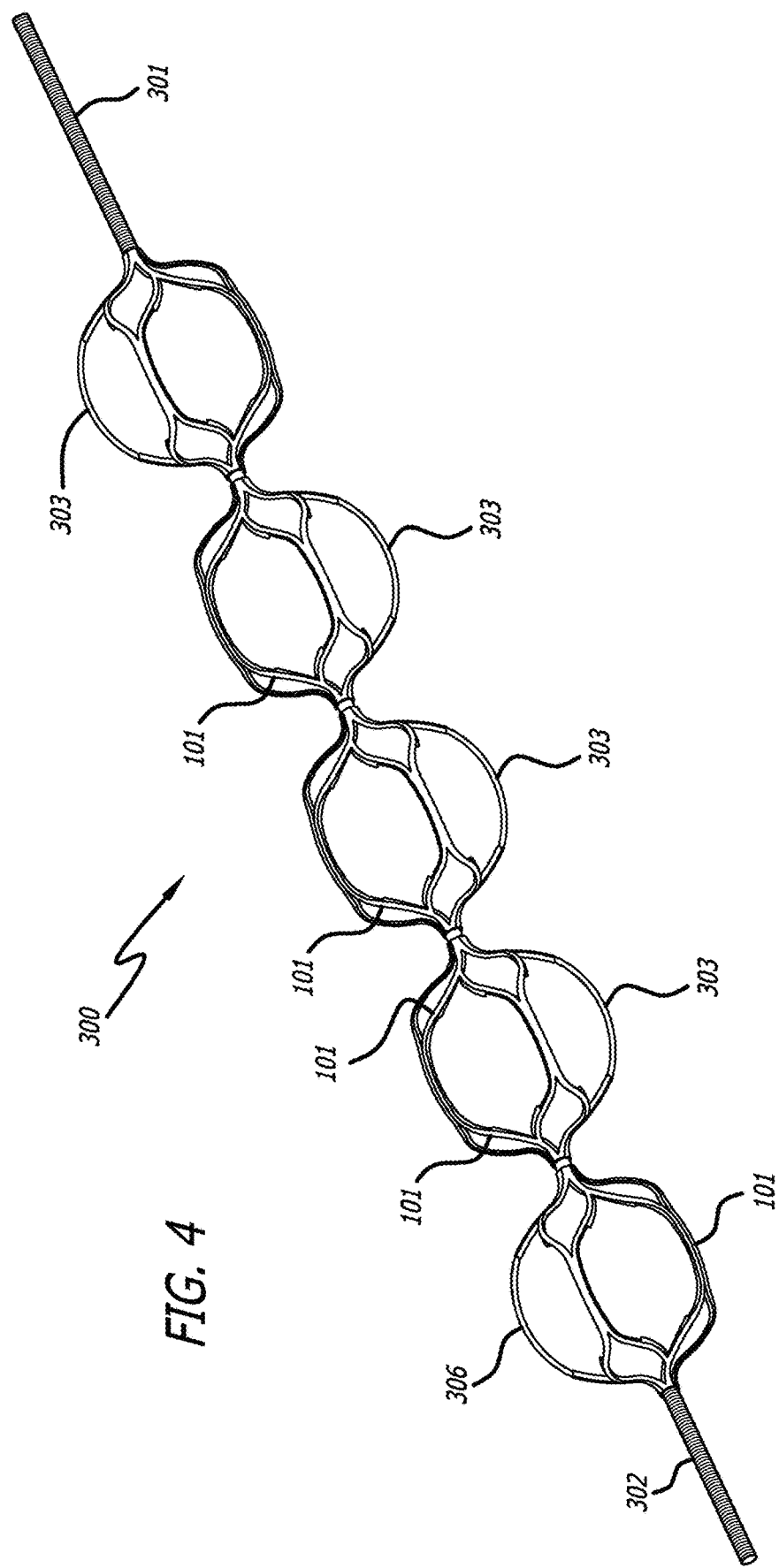
FIG. 4 is an obstruction removal device according to another embodiment of the present invention.

FIG. 4 illustrates an obstruction removal device 300 according to another embodiment of the present invention. The obstruction removal device 300 includes a proximal structure 301 connected to one or more engaging members 303. There may be a distal structure 302 attached to a distal-most engaging member (labeled as 306 for clarity, though it may be structurally the same or different as the other engaging members 303). The one or more engaging members 303 are connected to the proximal structure in such a way as to allow the one or more engaging members 303 to rotate independently of the proximal structure 301. The one or more engaging members 303 may be linked together to allow the engaging members 303 to rotate independently of each other as well, as discussed in more detail below. The obstruction removal device 300 is preferably pushed/pulled from one end of the proximal structure 301, thus the terms proximal portion structure and distal structure are used relative to the pushing/pulling end. Although five engaging members are illustrated in the figure, fewer or more engaging members can be used. Like all of the embodiments described herein, the engaging members 303 are constructed with one or more struts 101, as described above.

Figure 5:
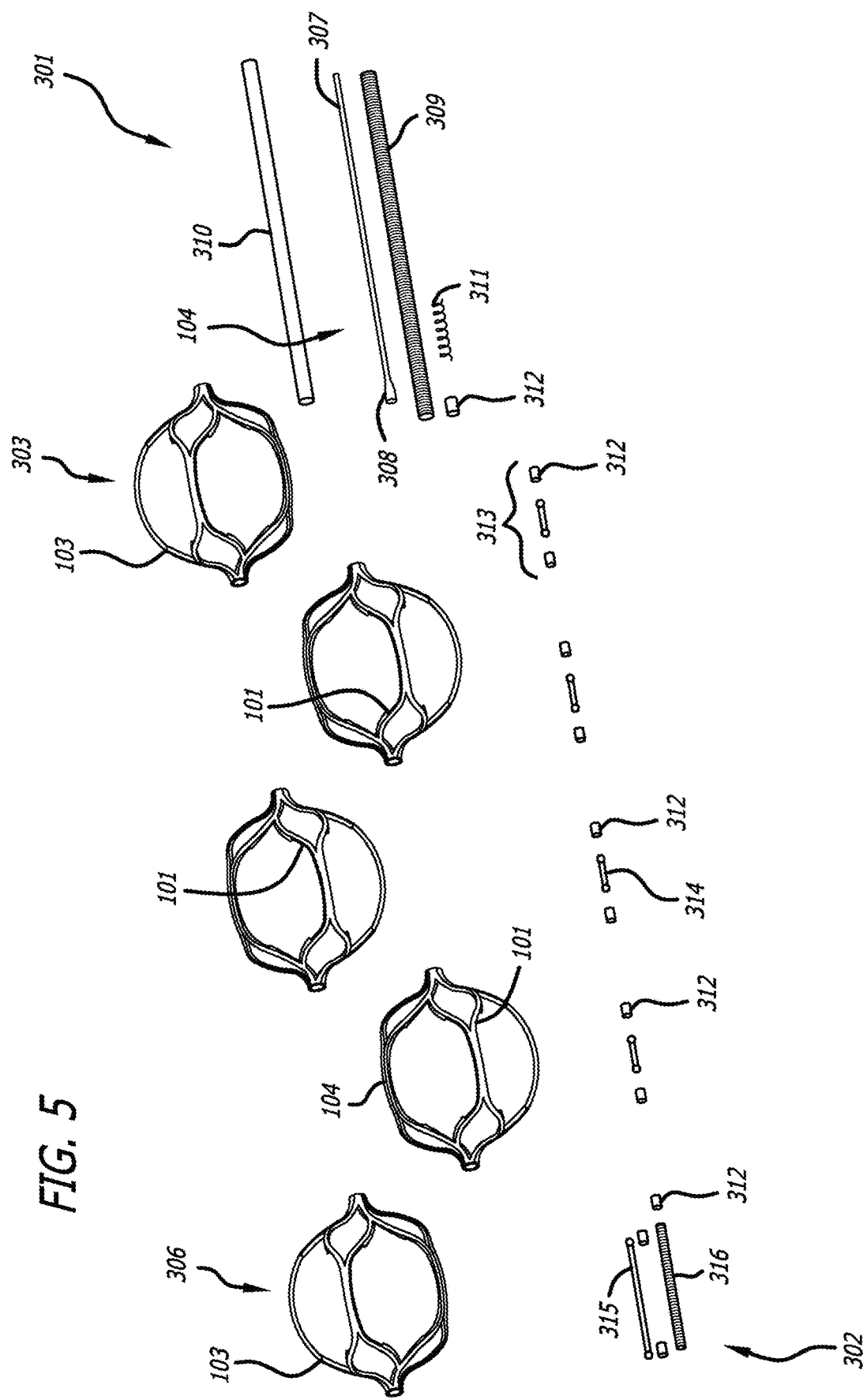
FIG. 5 is an exploded view of the obstruction removal device shown in FIG. 4.

FIG. 5 illustrates an exploded view of an embodiment of the obstruction removal device 300 of FIG. 4. The proximal structure 301 may include a core wire 307 which sits under a coil 309, which may sit under a tube 310. The core wire 307 includes a flared end 308. The core wire 307 may be made of nitinol, or a similar material, although other materials are within the scope of the invention. The coil 309 may be made of tantalum, or other radiopaque materials, although non-radiopaque materials may also be used. The tube 310 may be made of PET, or other polymeric material, although non-polymeric materials may be used as well. The proximal structure also includes another coil 311 which is preferably more gapped than coil 309, and can be made of a similar material. Coil 311 sits between core wire 307 and the over-coil 309, and helps center core wire 307 within coil 309. Proximal structure 301 is connected to a proximal engaging member 302, which can in turn be connected to another engaging member if more than one engaging member is used in the obstruction removal device.

The distal structure 302 includes a monofilament 315 which sits under a coil 316. Alternatively, multiple monofilaments can be bonded together to produce a monofilament structure 315. The monofilament 315 can be made of a stretch-resistant polymer such as Engage, although other materials may be used. The coil 316 may be made of tantalum, or other radiopaque materials, although non-radiopaque materials may also be used. Adhesive, preferably UV curable adhesive, 317 is used at both ends of the coil structure 316 in order to keep the monofilament 315 integral within the coil 316. In one example, the distal structure can act as a guidewire.

A distal structure 302 may be connected to the distal-most engaging member 306. This distal structure may be radiopaque in order to aid in imaging of the device during deployment. In the embodiment of FIG. 5, the coil of the distal structure 302 fits within the hole 103 of the distal-most engaging member 306, and a retaining piece 312 fits on the other end to keep the distal portion 302 integral with engaging member 306. The retaining piece is welded within the interior of the structure of hole 103. The engaging member 306 can still rotate. The retaining piece may be of a tubular construction, and may be made from nitinol, although similar materials can also be used. In order to aid in imaging, the retaining piece may be made from nitinol filled with a radiopaque material. Alternatively, the retaining piece may be coated with a radiopaque material to aid in imaging of the device during the procedure. Alternatively, the retaining piece may be made of a radiopaque material.

Figure 6:
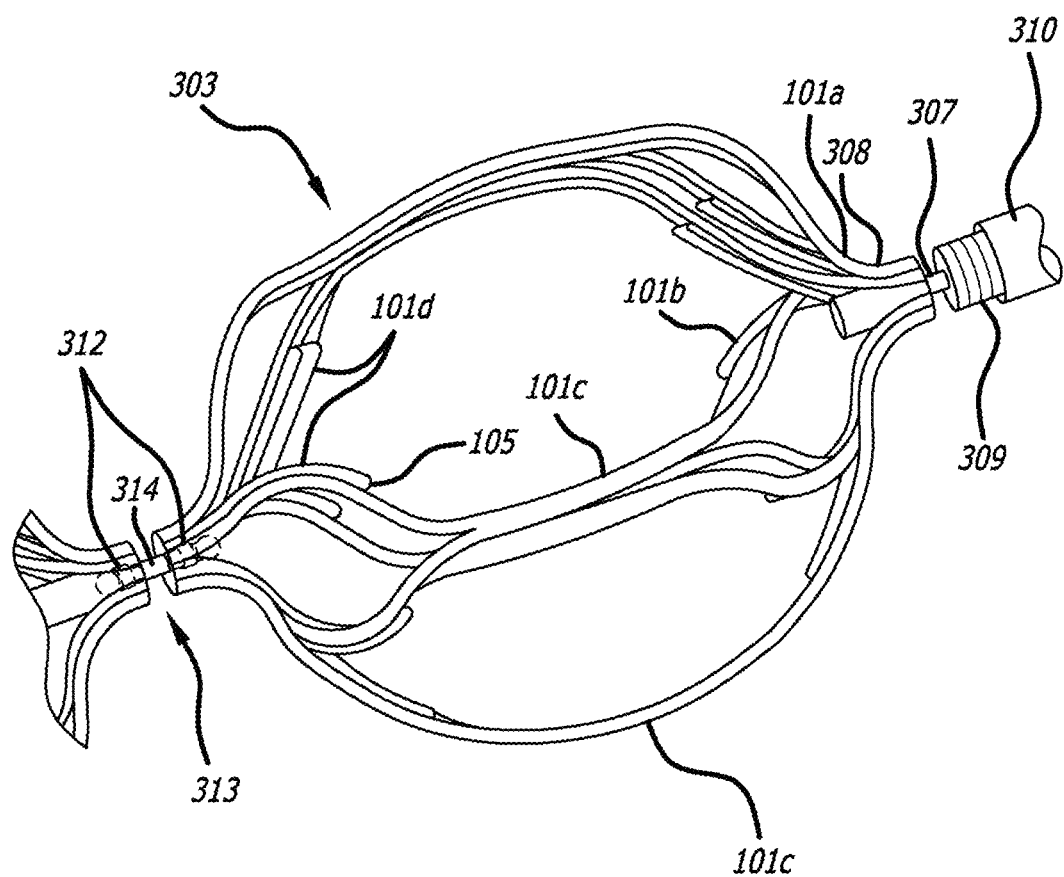
FIG. 6 is a magnified view of the proximal engaging member of the obstruction removal device of FIGS. 4 and 5.

The connection mechanism used to connect the engaging members together is shown in FIGS. 5 and 6. FIG. 6 illustrates the connection structure of engaging member 303, which is connected to the proximal structure 301 of the obstruction removal device.

The connection mechanism includes a link 313 with two flared ends 314, and retaining pieces 312. The link 313 may be made of stainless steel, although similar materials may be used. The flared ends extend within the opposing holes 103, 104 of the engaging members being connected, and the retaining piece 312 fits next to the flared end 314 to secure the link 313 within the hole of the engaging member. This connecting structure is used to connect the engaging members together, if more than one engaging member is used in the obstruction removal device. Retaining piece 312 is welded to the hole, and the link can rotate while secured within the hole of the engaging member. The engaging members may independently rotate.

Engaging member 303 is also connected to the proximal structure 301, as shown in FIGS. 5 and 6. The flared end 308 of the core wire sits past hole 104 of engaging member 303 and a retaining piece 312 sits over the core wire 307 to secure the proximal structure 301 to engaging member 303, where retaining piece 312 is welded within hole 104. A smaller, gapped coil 311 sits within the distal end of coil 309 and serves to help center the core wire 307 within the coil 309.

In one example, the connecting piece 313 is placed within the hole structure, and retaining piece 312 is welded into the hole over the connecting piece. The flared end 313 can subsequently be laser welded on the end of the connecting piece. In another example, the retaining piece 312 is welded into the hole and the connecting piece is placed within, and the flared end is laser welded. Although laser welding is specified, other similar heat treatment techniques can be utilized as well. This procedure can also be utilized at the end of core wire 307 to produce flared end 308, and to connect proximal-most engaging member 303 to the proximal portion 301 of the device. In one example, this procedure can be utilized at the end of the coil 316 when connecting the distal portion of the device to distal-most engaging member 306.

Each engaging member has a rotational component; this ability to rotate can aid in capturing the thrombus and navigating the vessel. This can also help limit the amount of endothelial denudation that may occur as the device is being pushed and/or pulled through the vessel, by helping to limit any excessive forces that build up due to excessive contact friction between the struts and the vessel wall. The engaging members may also be configured to have a more rounded, smoother profile (as illustrated in the figures) which would eliminate any sharp edges on the engaging members which may otherwise promote denudation due to high contact friction. Furthermore, due to the space between the engaging members, less material physically contacts the vessel than other designs which may utilize, for example, a longer one-piece clot engaging unit. Less material contacting the vessel will also serve to limit endothelial denudation during the clot removal procedure.

In one example, the proximal portion 301 of the obstruction removal device can include means to detach the engaging members from the obstruction removal device. The detachment means can be included on the portion of the proximal portion 301 contacting engaging member 303 (the proximal-most engaging member) and can include electrolytic, mechanical, thermal, or other means known in the art to induce severing and/or degradation of a linkage.

One or more of the engaging members may actively engage the clot, while other members can sit either distally beyond, or proximally before, the thrombus—depending on the size of the clot and the number of engaging members utilized on the device. Due to the potential variability in the individual shape and/or profile of each engaging member, as well as the number of engaging members used in the obstruction removal device compared to the size of the clot, one or more engaging members may sit distally past the clot and have a denser cell configuration to act as a filter for catching thrombus that may dislodge when capturing the clot utilizing the obstruction removal device.

The engaging member(s) which act as a filter may have a mesh configuration; said mesh configuration can be throughout the whole engaging member or be located on one particular side of the engaging member, in order to maximize the chances of catching loose thrombus without the thrombus dislodging. In one example, the engaging member(s) which act as a filter has a denser cell configuration on the more-distal portion of said member in order to catch thrombus dislodged from interaction of the more proximal engaging members with the clot. This arrangement can be useful when the more proximal engaging members interact with the clot and portions of the clot macerate. The more distal engaging members with the filter configuration can catch macerated thrombus that otherwise might accumulate in the bloodstream. The engaging members which act as a filter may be formed from nitinol, stainless steel, or similar materials.

Alternatively, they may be formed from laser cut polymers. Alternatively, these engaging members acting as filters may have an inverted braid configuration, or other basket-type configurations, or other configurations known within the embolic protection device art. One or more of the engaging members may also be composed of a thrombogenic material, or may be coated with a thrombogenic material in order to aid in the clot retrieval procedure, by promoting adhesion between the engaging member and the thrombus. Alternatively, an anti-thrombogenic material can be used, or an anti-thrombogenic coasting can be used in order to help dissolve a portion of the clot that is in contact with the engaging members. This can be useful with, for instance, retrieval operations involving a large clot.

Figure 7:
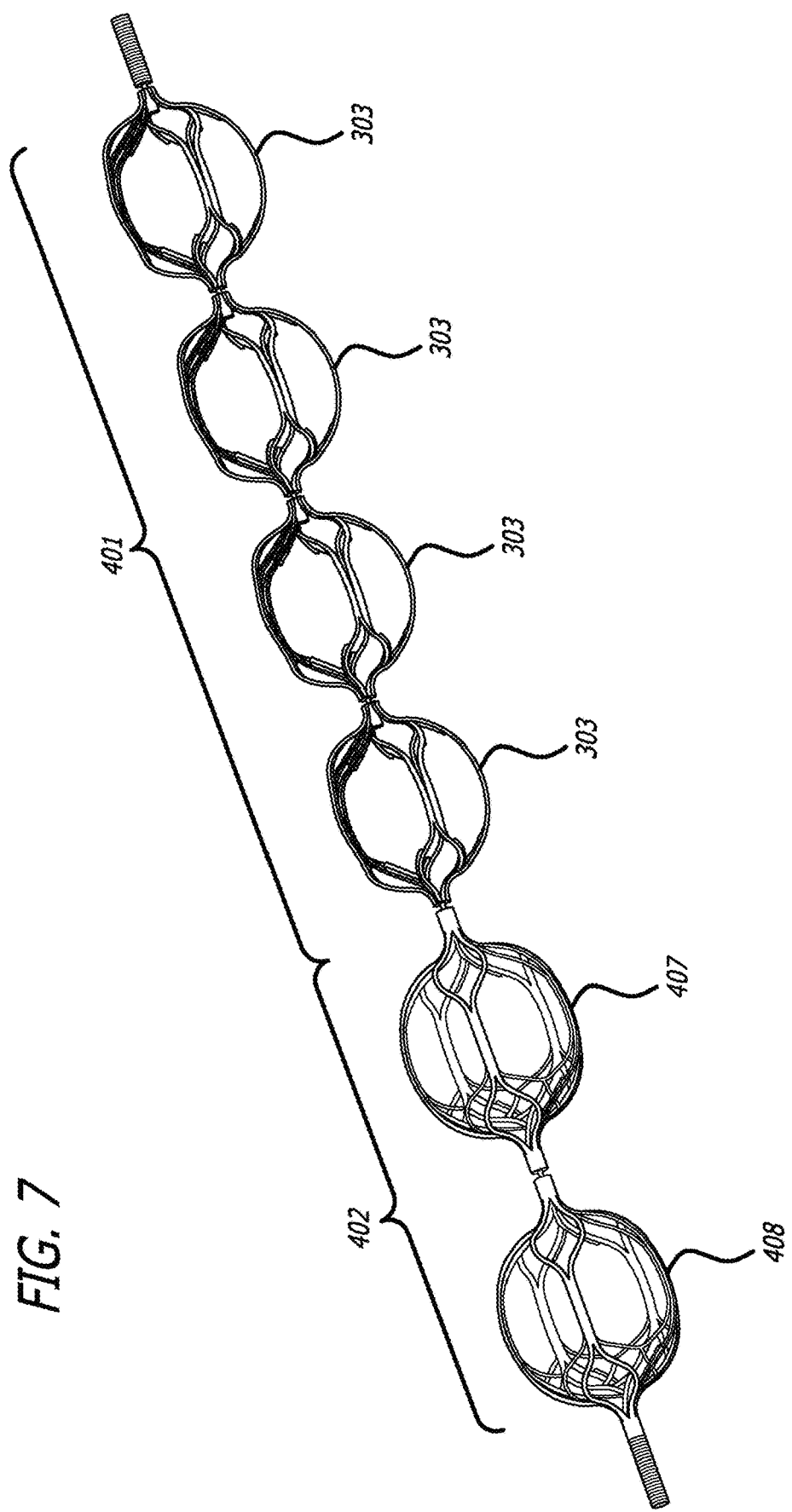
FIG. 7 is an obstruction removal device according to another embodiment of the present invention.
Figure 8:
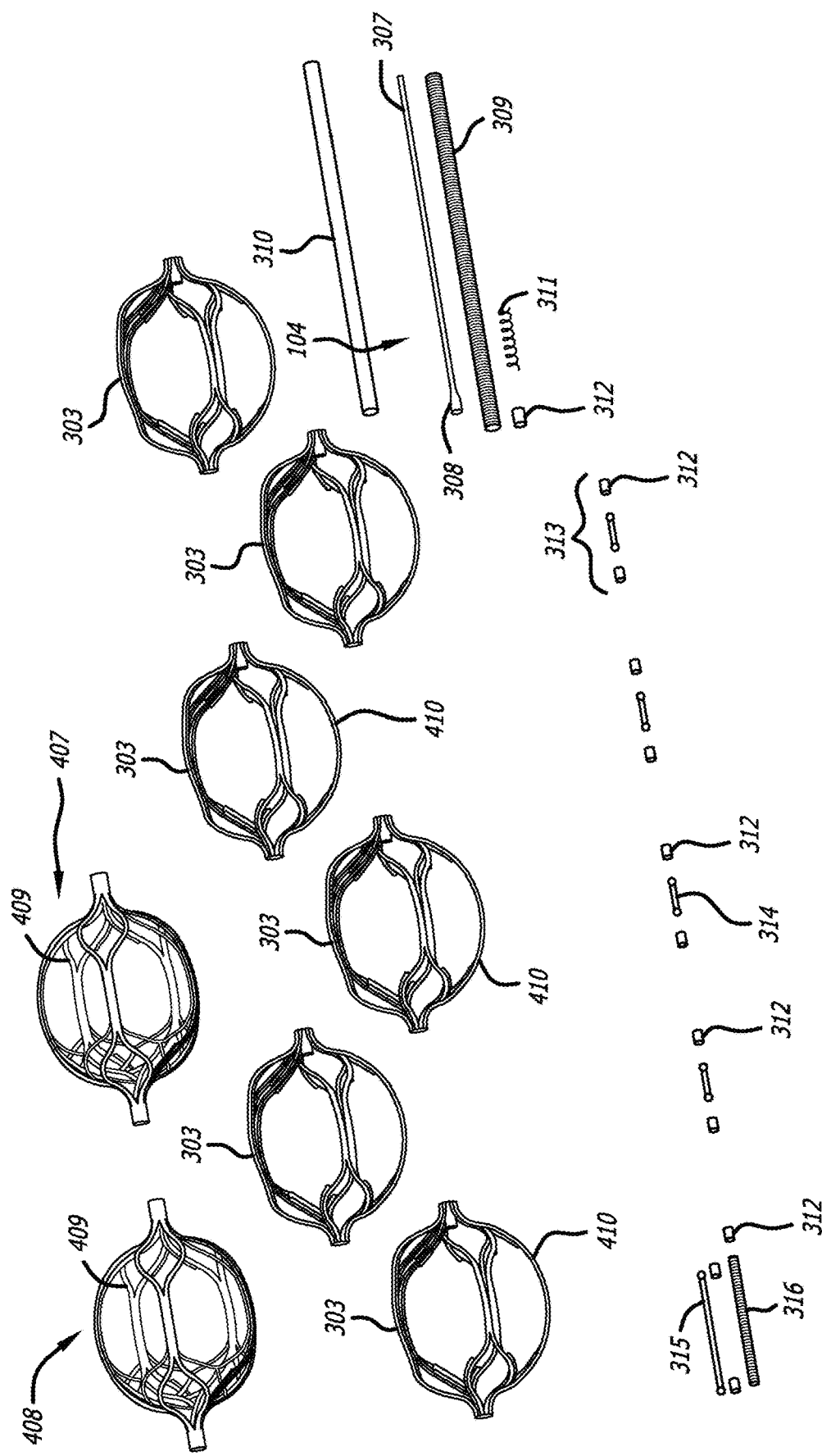
FIG. 8 is an exploded view of the obstruction removal device shown in FIG. 7.

FIGS. 7 and 8 illustrate another embodiment of the obstruction removal device utilizing one or more engaging members which act as a filter in order to catch thrombus that may become dislodged during the clot removal procedure. FIG. 7 illustrates the obstruction removal device, with a proximal portion 401 and distal portion 402. The proximal portion includes engaging members 303. The distal portion includes engaging members 407 and 408. The distal engaging members 407 and 408 have a denser cell configuration to act as a filter to trap dislodged thrombus which may shear off during the clot removal procedure, the clot removal procedure being generally described above. The denser cell configuration is due to an inner and outer structure used to form the engaging member, as illustrated in FIG. 8.

As illustrated in FIG. 8, the two distal engaging members 407 and 408 are each composed of an inner structure 409 and outer structure 410, where the inner structure may nest within the outer structure. The inner structure 409 and outer structure 410 which comprise the distal engaging members 407 and 408 may be made from laser cut nitinol, or a similar material. The proximal portion 401 and distal portion 402 are configured the same as the embodiment presented in FIGS. 4-5, as are the linkages between each of the engaging members, although this filtering engaging member structure can be applied to any of the engaging members presented in any of the presented obstruction removal device embodiments.

Figure 9:
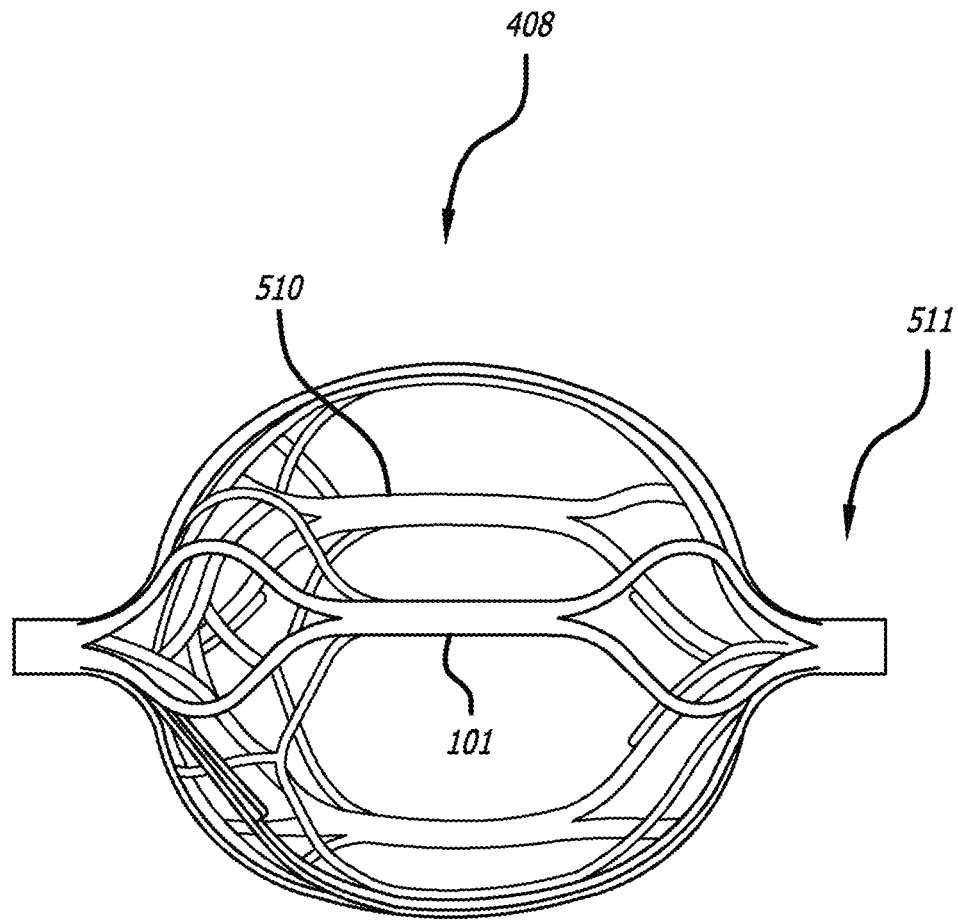
FIG. 9 is one of the distal engaging members used in the device shown in FIGS. 7 and 8.

The cell pattern may be slightly offset on the inner and outer structure in order to create a denser cell profile when the inner structure is nested within the outer structure. As shown in FIG. 9, the distal part 510 of the engaging member 408 has a denser cell profile than the proximal part 511 in order to catch dislocated thrombus which may escape during the clot removal procedure. This arrangement can be useful when the more proximal engaging members interact with the clot and portions of the clot macerate. The more distal engaging members with the filter configuration can catch macerated thrombus that otherwise might accumulate in the bloodstream. Although FIGS. 7 and 8 illustrate two engaging members having the inner and outer structure to act as a filter, more or fewer engaging members can have this filter structure.

In one embodiment for delivery of the device described in the previous embodiments, an obstruction removal device is sheathed within a delivery device, and the delivery device is delivered through a catheter. In one example, the delivery device can be a microcatheter. The delivery device is delivered to the site of the obstruction and then pulled back. Pulling back the delivery device unsheathes the obstruction removal device, such that the engaging members expand upon retraction of the delivery device.

Alternatively, the obstruction removal device is pushed out of the delivery device, which subsequently allows the engaging members to expand. Depending on the number of engaging members on the obstruction removal device, the size of the clot, and the location of delivery relative to the obstruction, some members may sit distally past, and/or proximally before, the obstruction. The obstruction removal device may be maneuverable via the core wire. Once the obstruction removal device engages the obstruction, the delivery device can be withdrawn to a point just past the distal end of the catheter, and then the catheter can be withdrawn. Alternatively, the obstruction removal device can be withdrawn from the vasculature by withdrawing the delivery device into the catheter, and subsequently withdrawing the catheter, or withdrawing the delivery device and/or obstruction removal device through the catheter. Alternatively, the catheter can be withdrawn wholly to remove the delivery device and obstruction removal device. In another example, the delivery device can be a hypotube.

In an alternative embodiment, the device may be delivered directly through the catheter, without being sheathed in a delivery device.

Figure 12:
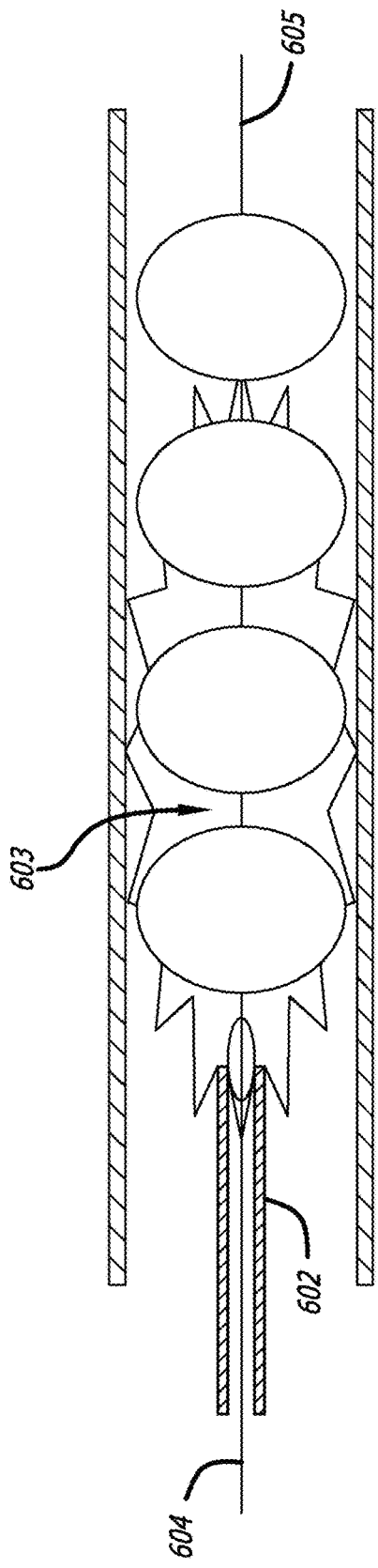

FIGS. 10-12 illustrate an example of a particular method for deploying the obstruction removal device. In this example, the delivery device 602 is delivered through the vasculature 600 to the site of the clot 601. The obstruction removal device 603 is pushed through the delivery device to the site of the clot. Although this particular example illustrates the obstruction removal device deployed in the middle of the clot, the device may be deployed within the clot, or in a location proximal or distal relative to the clot location. Some engaging members may sit distally past and/or proximally before the clot, depending on the size of the clot and the number of engaging members used on the obstruction removal device. Delivery device 602 is then retracted which allows the engaging members of the obstruction removal device to expand and interact with portions of the clot. The obstruction removal device 603 can be manipulated by the operator from the proximal portion 604 of the device. Once the obstruction removal device has secured the clot, the device can be withdrawn as described above. Aspiration may also be used to aid in the clot/obstruction removal procedure. FIGS. 10-12 illustrate a particular example for illustrative purposes. Other delivery methods are contemplated within the scope of the invention, such as pushing the obstruction removal device from the delivery device.

The engaging members may all be the same size, may all be different sizes, or may have some engaging members sized differently from others. In one example, the diameter range for spherically shaped engaging members may be between 1-12 millimeters. In another example, a diameter range of 3-6 millimeters is used.

Figure 13:
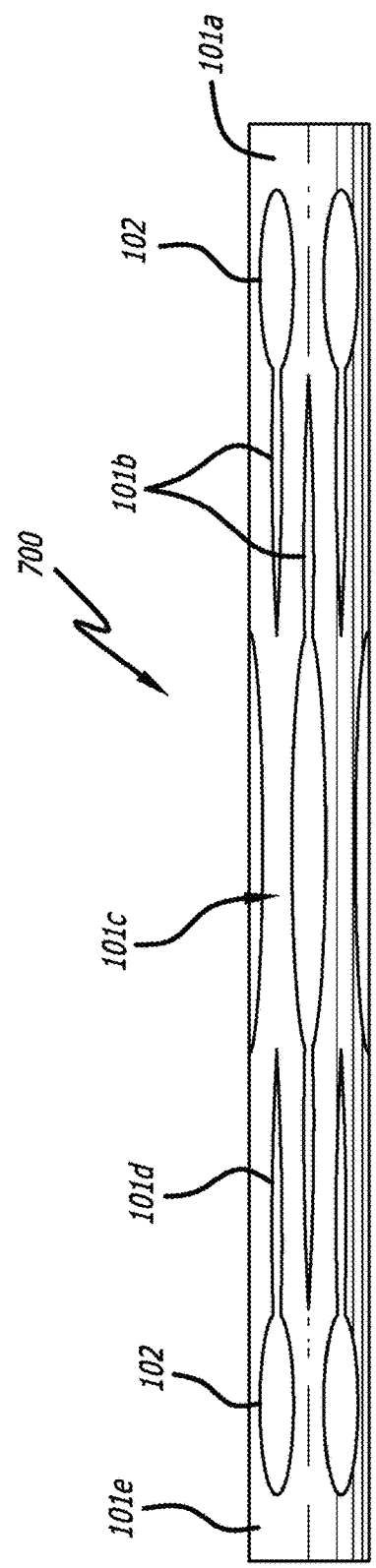
FIG. 13 illustrates a hypotube used to create an engaging member
Figure 14:
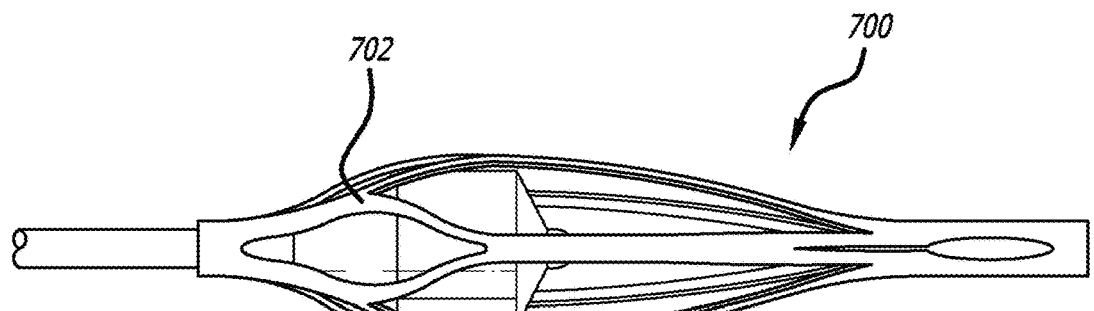
FIGS. 14-16 illustrate a process used to help set the final shape of an engaging member
Figure 15:
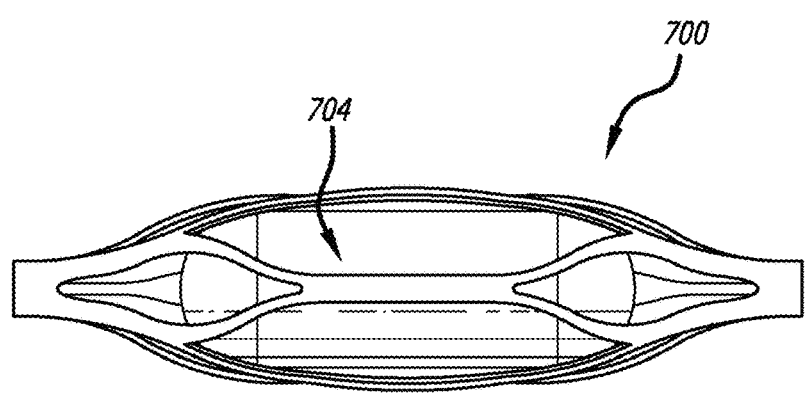
Figure 16:
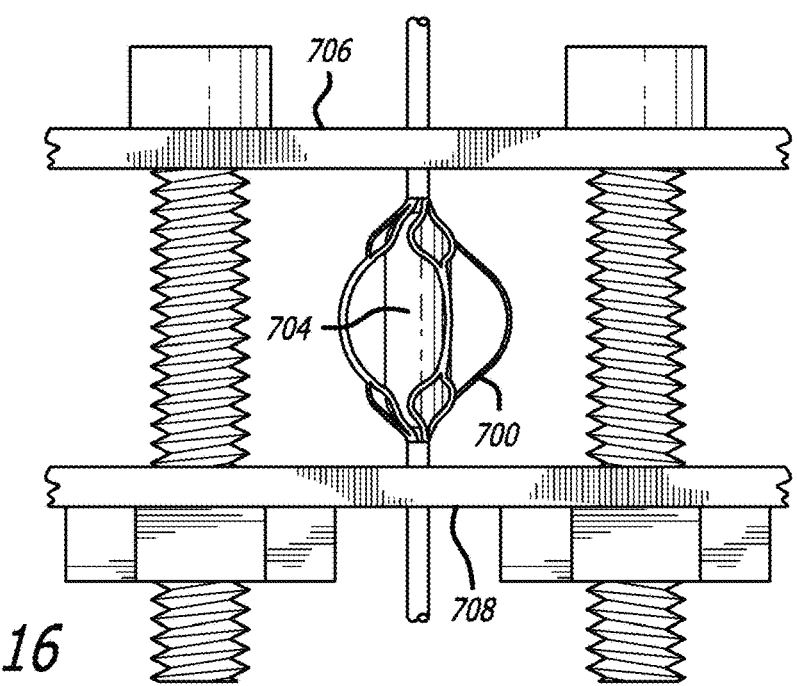

The engaging members are formed from a hypotube which is laser-cut into a particular pattern based on the shape of the struts 101 and cells 102. This hypotube 700 is shown in FIG. 13. The hypotube is heat treated, in one example the hypotube can be heat set at 530-550 degrees Celsius for 5 minutes. The hypotube is subsequently quenched in water to cool. An expansion plunger 702 is then inserted and used to expand a portion of the hypotube (see FIG. 14). The expanded hypotube is then heat-set to this expanded shape. In one example, it is heat set at 530-550 degrees Celsius for 3 minutes. The expanded hypotube is subsequently quenched in water. Based on the size of the engaging member, the expansion plunger and subsequent heat treatment step can be used on multiple portions of the engaging member, where each section is heat set after expansion. An expansion pin 704 is subsequently inserted within the hypotube to help expand the walls of the hypotube (see FIG. 15). The expanded hypotube 700 is placed in a fixture. The fixture includes two plates 706, 708. Threaded rods connect the plates, and the plates have an external mounted nut. The nut can be tightened to compress the plates together in order to further expand the hypotube. Once the appropriate shape is set, the expanded hypotube can be heat treated (in one example, heat treated at 530-550 degrees Celsius for 5 minutes) and quenched to set the shape of the engaging member.

The engaging members are subsequently pickled, etched, and electropolished to set the final shape of the said members. The obstruction removal device is then assembled together with the one or more engaging members. Though the engaging members are heat-set and treated into an expanded shape, they still retain a high degree of shape memory due to factors such as material properties and strut thickness. Thus, the engaging members will adopt an expanded shape when not restrained (i.e. not sheathed in a delivery device) and will adopt a contracted shape similar to the initial hypotube shape when restrained (i.e. sheathed in a delivery device).

The previous embodiments generally disclosed engaging members in which all of the struts span the length of the engaging members. Alternative embodiments can utilize some struts that do not span the length of the engaging members. For instance, those partially-extending struts can extend only along a proximal end of the engaging member and vary in length relative to each other. These partially-extending struts can help augment clot retention capability of the overall obstruction removal device.

Figure 17:
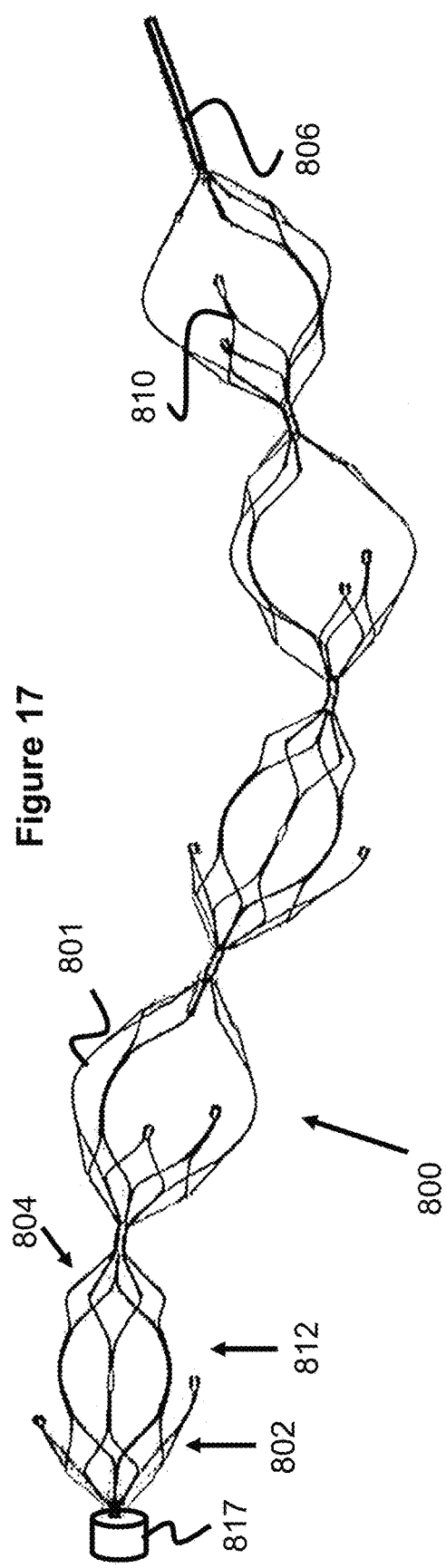
FIG. 17 illustrates an obstruction removal device comprising engaging members where the engaging members include some struts than span the length of the engaging member and some struts that do not span the length of the engaging member.
Figure 18A:
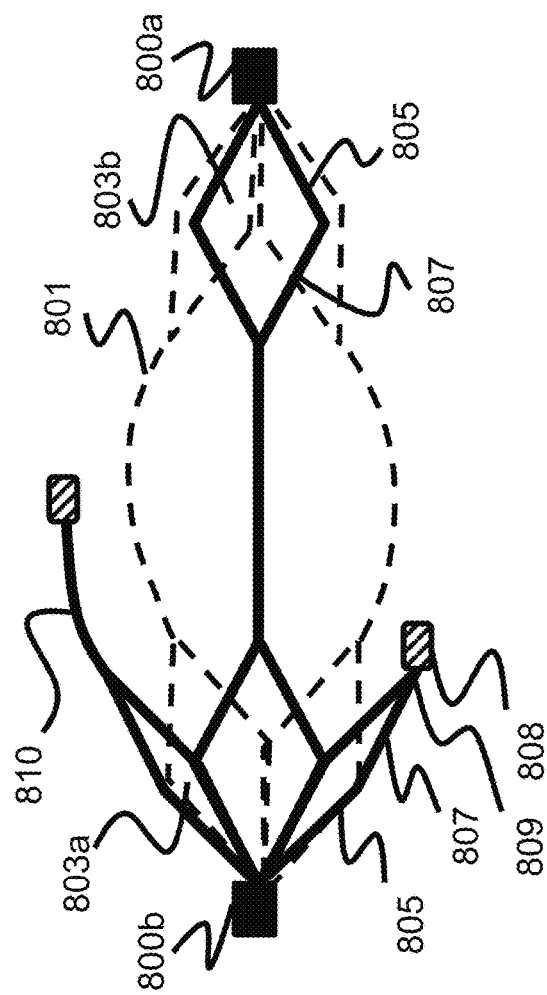
FIGS. 18a, 18b, 18c, and 18d illustrate various views of the obstruction removal device of FIG. 17.
Figure 18B:
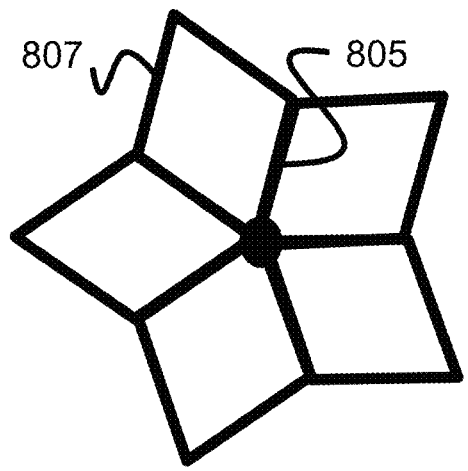
Figure 18C:
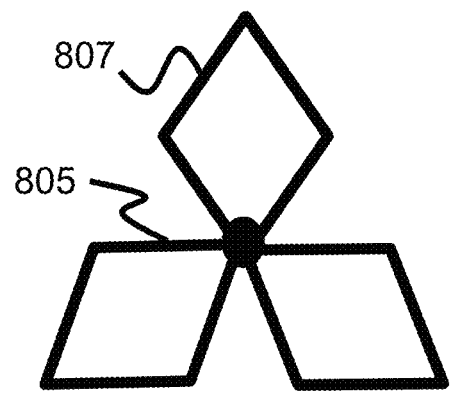
Figure 18D:
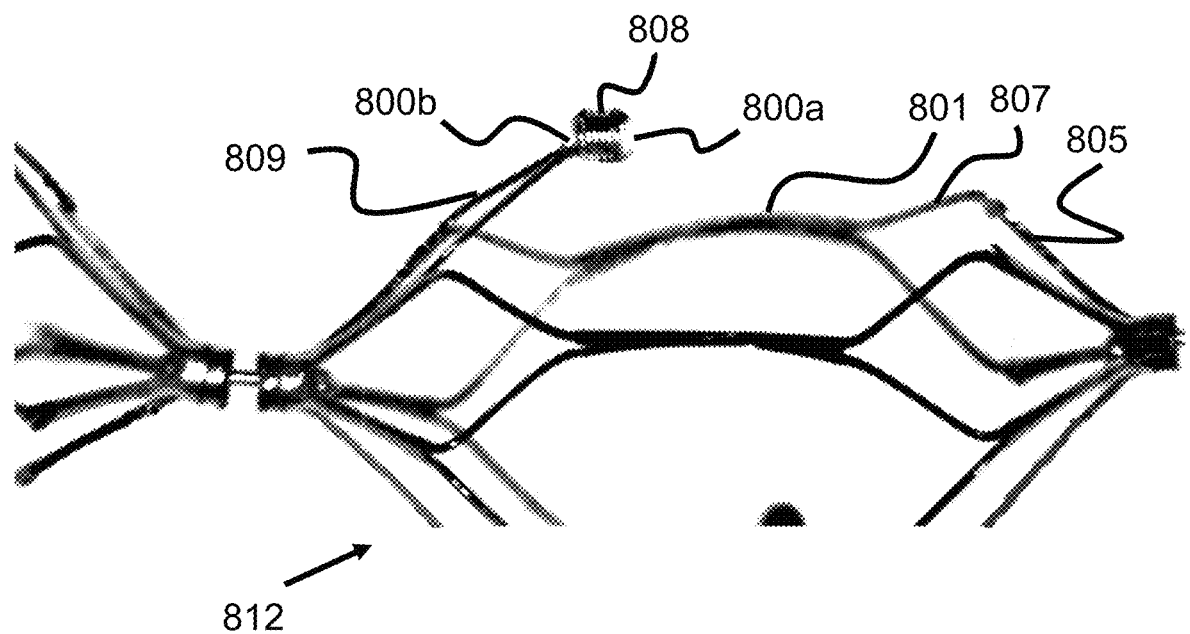

Please note, for the sake of the embodiments presented in FIGS. 17-18d, unless otherwise indicated, anything on the left side of the figures would be considered proximal or in the direction of where vascular access was obtained while anything on the right side of the figures would be considered distal or in the direction of further placement within the vasculature.

FIGS. 17, 18a, 18b, 18c, and 18d illustrate one example embodiment of an obstruction removal device 800 where some struts (e.g., struts 801) connect at proximal and distal ends of the engaging members 812 and other struts (e.g., struts 810) only connect at one end of the engaging members 812, leaving their other end unconnected/freely floating.

This strut configuration can be seen best in the side view of FIG. 18a, the proximal end view of FIG. 18b, and the distal end view of FIG. 18c. Specifically, the proximal and distal ends of the engaging members 812 have a plurality of smaller struts 805, 807 that generally form a plurality of "flowering" or inclining diamond or loop shapes. These diamond or loop shapes are formed of a number of inner struts 805 that are connected to form a from proximal or distal aperture/hole 800a/800b and a number of outer struts 807 connected to these inner struts. For example, the proximal end of the engaging member 812 includes five diamond shapes 803a and the distal end includes three diamond shapes 803b. Put another way, the proximal end of the engaging member 812 includes five primary or inner struts 805 radially extending from a distal end of the engaging member. Each of those struts split into a "Y" shape of secondary or outer struts 807, with the distal ends of each secondary struts 807 merging together with adjacent secondary struts 807 from a different, adjacent primary strut 805.

The five proximal diamond shapes 803a connect to either a lateral strut 801 that spans between the distal diamond shapes 803b, or a partial lateral strut 810 that does not span the full length to the distal diamond shapes. As shown in FIG. 18a, some struts can also terminate right where outer struts 807 merge—shown as smaller retained lateral strut 809. In this way, some struts 801 span between the proximal diamonds 803a and distal diamonds 803b, and some do not.

This configuration can be made in various ways. In one method, the struts are formed from the hypotube in FIG. 13, which is used to create the engaging member strut shapes shown, for example, in FIGS. 7-9. Once the engaging member is expanded to take on its full shape, some of the struts are then cut to create the shape shown in FIGS. 17-18. In another method, the hypotube itself which is used to create the engaging member may have cut-out strut sections so that the finalized engaging member takes on the shape shown in FIGS. 17-18d.

In one embodiment, one end of the engaging member 812 can have a larger retained strut-section (i.e., more "diamond" shapes) than the other end—as shown in FIGS. 17-18d. In FIGS. 17-18d, the left side 802 of the engaging member 812 (also known as the proximal side of the engaging member, since the pusher is connected to the left-most engaging member for the purposes of the figures) has a larger number of struts 805, 807 than the right (or distal) side 804 of the engaging member 812. As best seen in FIGS. 18a and 18d, this configuration can be made by cutting a preformed lateral strut 801 near the point they would normally merge into secondary struts 807. On the other side of the engaging member 812, the strut pairs can be cut at an earlier termination point leaving one end with a larger retained partial lateral strut 810 and the other end with a smaller retained lateral strut 809. This configuration further enables better proximal gripping of the clot as the device is retracted into the larger guide or access catheter 817 to evacuate the device after clot retrieval is accomplished.

In other embodiments, the distal end of the engaging member 812 is attached to the larger retained partial lateral strut 810. This configuration creates a distal net structure to help ensure the ensnared clot does not travel distally during the clot capture procedure. Alternatively, the individual engaging members can be customized such that some engaging members have a larger proximally-retained strut sections, while other engaging members have larger distally-retained strut sections. In one example, a clot retrieval device can utilize a proximal-most engaging member with a larger proximally-retained strut section and a distal-most engaging member with a larger distally-retained strut section. This configuration would balance the benefits between augmenting clot retention during retraction through a catheter, while further minimizing the risk of distal clot migration during the clot retrieval procedure.

Figure 19:
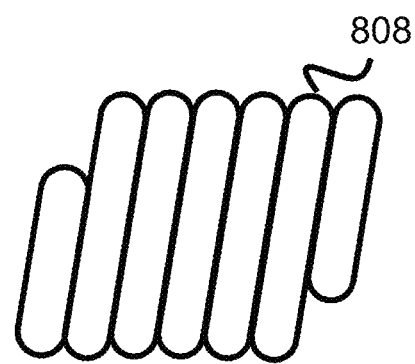
FIG. 19 illustrates a marker coil used on the engaging member struts of FIGS. 17-18d.

As best shown in FIGS. 18a and 18d, the retained partial lateral struts 809, 810 terminate with a marker coil 808. The marker coil 808 is separately shown in FIG. 19 and has a diameter or thickness that is greater than the partial lateral struts 809, 810. The marker coil 808 is used to aid in imaging the clot retrieval device and note the location of the engaging members and whether said engaging members are in an expanded or collapsed shape. The marker coils 801 can be composed of a variety of radiopaque materials including gold, platinum, tantalum, tungsten, or palladium. Additionally, the marker coil can take on a variety of configurations including a braid, band, or tube. In one example, the marker coil 808 is connected onto the struts by using UV glue in the internal diameter of the marker. FIG. 18d shows rounded/ball-like projections 808a, 808b on the proximal and distal ends of the marker band. In one embodiment, UV glue or laser welding is used in order to create these ball elements which create a secure locking interface between the struts and the marker coil. The marker coil 808 and ball-like projections also provide a larger contact surface interface than the end of the strut sections (as shown in FIG. 18d) and provide a larger contacting surface to help engage and retain the clot. Note, the marker coil 808 can alternately be located on the lateral strut 801 at a location adjacent to termination of either partial lateral strut 809 or 810.

Please note, though the embodiments of FIGS. 17-18d show individual linkages between each pair of engaging members (similar to the embodiments of FIGS. 4-8), the engaging members may alternatively sit along a common structure (similar to the embodiment of FIG. 3).

The following embodiments related to obstruction removal devices in which the engaging members strut shapes are configured to help shear thrombus or clot from a vessel wall and can be useful in scenarios involving calcified thrombus.

Earlier embodiments of engaging members, such as those shown in FIGS. 1-9, utilize struts 101 comprising a lengthy strut section 101c which spans the majority of the length of each engaging member. These struts are aligned in a generally longitudinal orientation in the blood vessel wall thereby mitigating the risk of the struts shearing off the vessel wall surface and damaging the vessel when pushed or pulled. However, in some circumstances it may be desirable to have an obstruction removal device that has higher shearing force; for example, in situations involving calcified thrombus or clot attached to the vessel wall in which it a large amount of force is necessary to remove or scrape the clot or thrombus from the vessel wall. An engaging member utilizing twisted lateral strut elements rather than straight strut elements would provide this higher shearing force.

Figure 20:
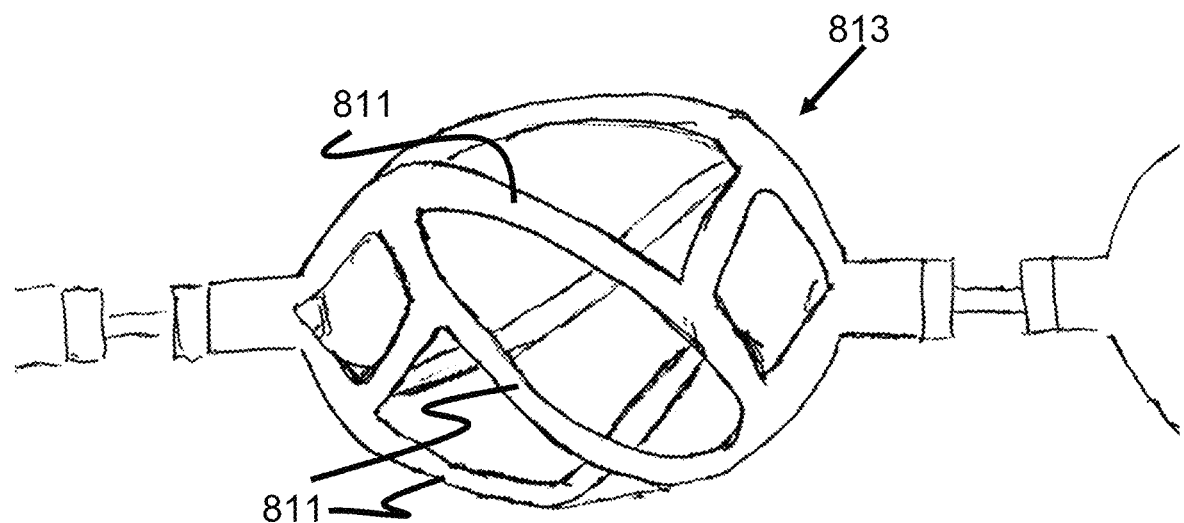
FIG. 20 illustrates an engaging member used in an obstruction removal device where the engaging member has a twisted strut pattern.

The engaging member 813 shown in FIG. 20 utilizes several lateral strut elements 811 that are not longitudinally aligned between the proximal and distal ends of the member 813, but rather are aligned at an angle (e.g., 1-89 degrees, for instance 45 degrees) relative to a proximal-distal axis of the member 813. This contrasts with the more axially-longitudinal or "straight" strut elements 101c shown in FIGS. 1-9. These twisted lateral strut elements 811 create greater surface contact between their edges and the vessel wall or clot when pushed or pulled. In this respect, the lateral strut elements 811 can better scrape the vessel walls to remove hard or calcified clot/thrombus which may be attached to the vessel wall. In several embodiments, the engaging members are capable of rotation and independent rotation, so as the engaging members rotate, different parts of the strut contact the vessel further augmenting the scraping effect against clot/thrombus.

Figure 21:
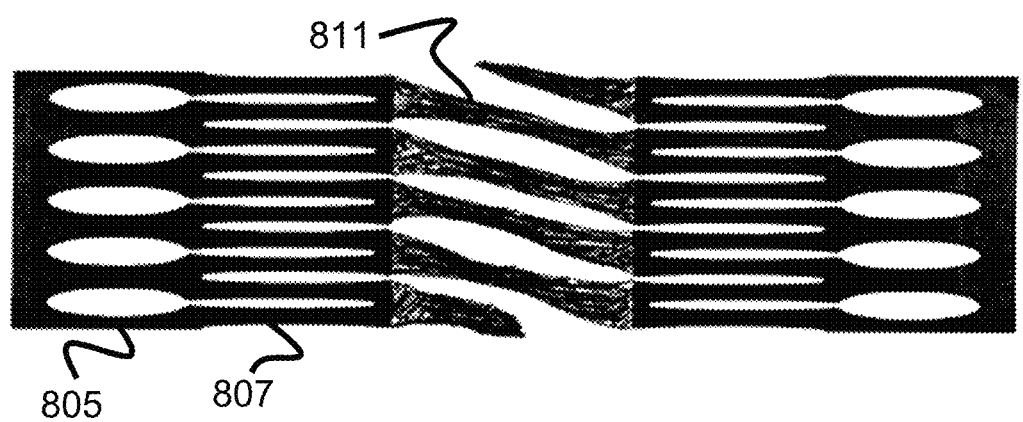
FIG. 21 illustrates a hypotube used to create the twisted strut pattern engaging member of FIG. 20.

FIG. 21 shows a hypotube shape (shown flattened for illustrative purposes) with twisted lateral strut elements 811 in the middle which correspond to the twisted strut elements of the engaging member. In one embodiment, a tube is laser-cut to create the strut shapes of FIG. 21. In one embodiment, a flat sheet is laser-cut to create the strut shapes shown in FIG. 21, then the sheet is rolled around a mandrel and the two ends of the sheet are welded together to create the circular engaging member shape of FIG. 20. Compared to the hypotube of FIG. 13 which utilizes substantially straight primary straight sections 101c (i.e., those struts that run the majority of the length of the engaging element), the hypotube of FIG. 21 utilizes angled strut elements 811 to create the twisted/angled configuration of FIG. 20. While in FIG. 13, strut elements 101d and 101c sit along the same plane, in FIGS. 20-21, strut elements 811 are angled and do not sit along the same plane as merging strut pairs 801d.

Other embodiments of an obstruction removal device can utilize multiple engaging members which sandwich the clot from either side to engage and retain the clot. Please note for the following figures, unless indicated otherwise, anything to the left would be considered distal or in the direction further downstream within the vasculature while anything to the right is considered proximal or in the direction where vascular access is gained. FIGS. 22-25 show this obstruction removal device 900, which utilizes a distal fixed clot disruptor structure 908 which is located distal to a clot 910 and a proximal sliding clot catcher structure 906 which is positioned proximal to the clot 910. The two structures 906, 908 are connected on a distal portion 902 of a pusher or core wire 901. The distal clot disruptor 908 is fixed or bonded to the distal portion 902 of the core wire 901 and the proximal clot catcher structure 906 can slide along the distal portion 902 of core wire 901, but is prevented (e.g., via a radially enlarged stop portion) from sliding along the entirety of core wire 901. This sliding can be enabled in a number of ways, for instance in one embodiment, one end 906a of proximal clot catcher structure 906 can be connected to a sleeve or band which is positioned over and can slide relative to the core wire's distal portion 902.

Various methods can be used to limit the amount that proximal clot catcher structure 906 can slide. In one embodiment, a proximal and/or distal stop 906a can project out from the core wire's distal portion 902 in order to limit the amount that the proximal clot catcher structure 906 can slide. A proximal stop limits the amount the clot catcher structure 906 slides proximally, a distal stop limits the amount the clot catcher structure 906 slides distally. In another embodiment, no stop structure is present, however the proximal clot catcher structure 906 can slide freely solely over core wire's distal portion 902. This can be accomplished if the core wire's distal portion 902 is smaller than the remaining proximal portion of core wire 901 such that the sliding catcher structure 906 has enough clearance to slide over distal core wire section 902 but not the rest of core wire 901, since said core wire 901 will be oversized compared to distal core wire section 902.

Figure 22:
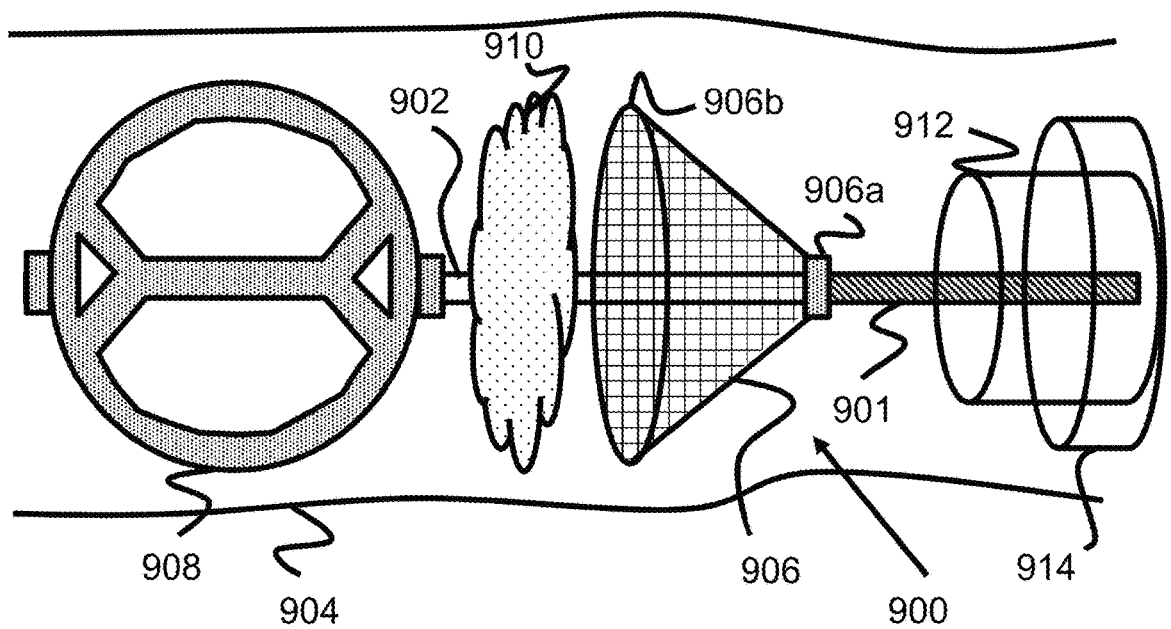
FIGS. 22-24 illustrate an obstruction removal device comprising a catch element and an engaging member.
Figure 23:
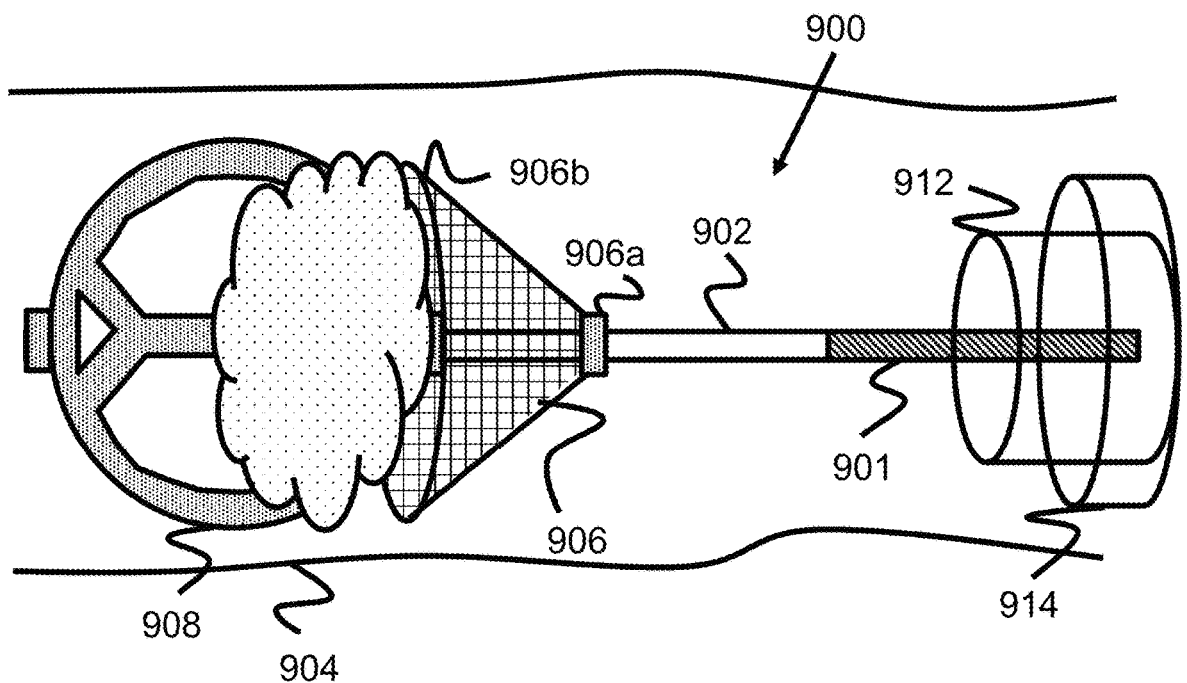

The method of use of the obstruction removal device embodiment 900 of FIG. 22 is described as follows. The physician typically uses a larger guide or access catheter as a sheath for a smaller microcatheter 912 which contains the obstruction removal device 900. The physician advances the microcatheter 912 in the vessel 904 and through clot 910 and then retracts the microcatheter 912 to expose the clot/obstruction retrieval device 900, such that the distal disruptor structure 908 is located distal to clot 910. The physician then pulls core wire 901, which causes the distal disruptor structure 908 to engage and push against clot 910. Proximal catcher structure 906—which has a degree of sliding movement but is proximally limited in its movement (as discussed above)—may move proximally once it contacts clot 910 but will fully engage the clot once stopped, as shown in FIG. 23. Once the clot 910 is retained by the obstruction removal device 900, the physician can retract core wire/pusher 901 so that the removal device 900 is sheathed inside a larger guide or access catheter 914 and then the whole system is removed from the patient vasculature.

The proximal clot catch structure 906 and distal clot disruptor 908 can take on various shapes or designs. One embodiment of an obstruction removal device 900 is illustrated in FIG. 22 in which the distal clot disruptor 908 is shaped like the engaging member of FIGS. 1-2; however, other embodiments can utilize a distal clot disruptor 908 shaped like any of the engaging members shown and described in other engaging member embodiments presented. In one embodiment, proximal clot catch structure 906 is a mesh of braided wires and the proximal end of catch structure 906 is closed but slidable over the core wire while the other end 906b is open to accommodate clot 910. In other embodiments, proximal clot catch structure 906 is a polymeric structure or even a stent where the proximal end of the stent is secured via a retention means (e.g., a marker band) over the core wire in a slidable manner while the other end of the stent is flared or open to accommodate clot 910. Mesh and polymeric stents are described in US20130245745 which is hereby incorporated by reference in its entirety and the proximal clot structure can be one of the stents described therein.

Figure 24:
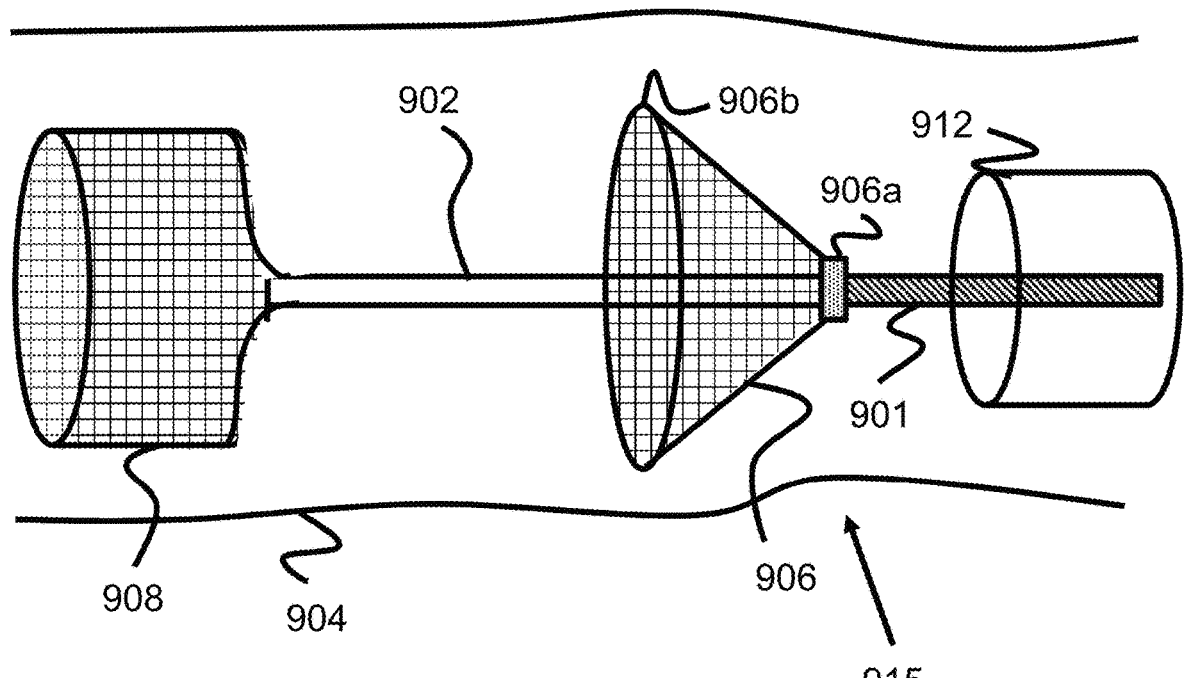

In another embodiment of an obstruction removal device 915, a mesh or polymeric stent, including those previously incorporated by reference are used for the distal clot disruptor 908, in which the proximal end of the stent is bonded to the core wire 902—as shown in FIG. 24. In another embodiment, the proximal clot catch structure 906 takes on the configuration of a vessel filter or embolic protection device (EPD). EPD's are often placed downstream of a stent or balloon in a procedure to open a clogged blood vessel, where the EPD is dispatched downstream prior to the stent or balloon placement in order to catch thrombus dislodged during the procedure. Generally a distal end of the EPD/filter would be bonded to or over the core wire 902 while the proximal end is an open mouth, since the EPD/filter is placed distal to the treatment site. Here, if an EPD/filter is used for the proximal clot catch structure 906, the proximal rather than distal end of the EPD/filter is bonded in a slidable manner over the core wire since the distal mouth of the filter should be open to help entrap the clot. EPD/vessel filters are described in US2014/0288588, which is hereby incorporated by reference in its entirety. Any of the EPD/vessel filters described therein could be used for proximal catch structure 906.

Figure 25:
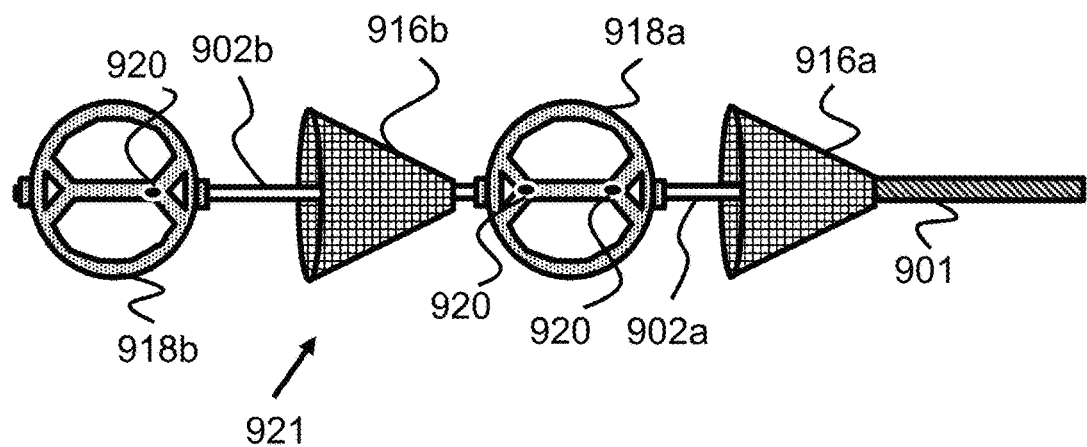
FIG. 25 illustrates an obstruction removal device comprising multiple catch elements and multiple engaging members.

FIG. 25 shows an embodiment of an obstruction removal device 921 utilizing multiple members along a core wire. An obstruction removal device 921 with multiple members capable of engaging the clot is useful to remove larger clots, or a clot which is hardened or calcified and would be otherwise difficult to remove. In this example, there are two clot catcher structures 916a, 916b and two clot disruptor structures 918a, 918b placed in an alternating manner (e.g. from proximal to distal: a proximal clot catcher 916a, then a first clot disruptor 918a, then a second clot catcher 916b, then finally a distal-most second clot disruptor 918b). In one example, the proximal clot catcher 916a is slidable, the first clot disruptor 918a is fixed or has a limited degree of movement, the second clot catcher 916*b* is slidable, and the distal-most second clot disruptor 918*b* is fixed.

For embodiments where first clot disruptor 918*a* is capable of some limited degree of motion, there are several ways to allow this. In one example, the proximal and distal ends of the first clot disruptor that sit over the core wire distal section 902 are oversized and the core wire distal section 902 can have built in enlargements so that the first clot disruptor ends will hit the enlargements to limit movement in either direction. In another example shown in FIG. 25, the core wire distal section 902 is segmented rather than continuous. A first leg 902*a* of the core wire distal section 902 terminates in a ball or enlarged projection 920 within the first clot disruptor structure 918*a*. A second leg 902*b* spans between first clot disruptor 918*a* and second clot disruptor 918*b* and terminates in a ball or enlarged protection 920 within said second clot disruptor 918*b*. The enlargements 920 limit the movement of each clot disruptor since the clot disruptors cannot move once the proximal or distal ends of the clot disruptors contact the enlargements. This functions like the obstruction removal device of FIGS. 4-6, in which engaging members are separated by individual links 313 with flared ends which limit translation of the engaging members. Please note, even in the absence of any structures limiting movement of the various objects on the core wire, the structures are already limited in movement since each structure cannot move past the neighboring structure. For example, the proximal clot catch 916*a* can move but the end that slides over the core wire cannot move past the proximal end of the first clot disruptor 918*a*.

Various versions of the embodiment of FIG. 25 could utilize more clot disruptors and/or more clot catcher structures, or different combinations of clot disruptors and clot catcher structures. The segmented core wire system described above, the single core wire enlargement section described above, or combinations of these two systems can be used to allow limited movement of the various structures on the obstruction removal device.

Figure 26:
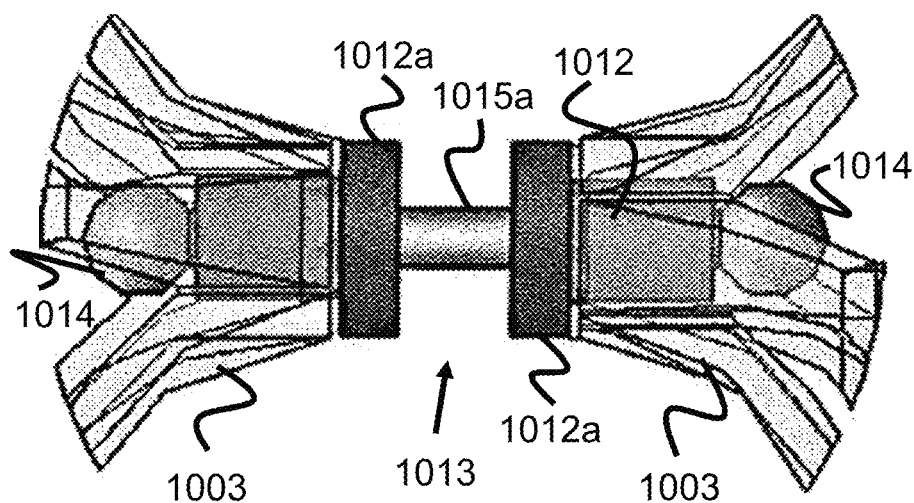
FIG. 26 illustrates a linkage system used between engaging members of an obstruction removal system, where the engaging members are capable of independent rotation.

Many of the obstruction removal device embodiments presented thus far have utilized engaging members which are capable of independent rotation. Referring to FIG. 26 (which offers another view of the linkage elements originally shown in FIGS. 5-6 connecting the engaging elements), this is possible by utilizing a linkage 1013 between pairs of engaging members. Linkage 1013 includes two flared ends 1003 (e.g., enlarged spherical regions) and a retaining piece 1012 (e.g., a cylinder or sleeve) which operate to limit translation of the engaging elements while allowing said engaging elements to rotate independently of each other. Two marker bands 1012*a* can also optionally be placed at either end of the gap 1015*a* between the engaging elements to further aid in imaging. The marker bands 1012*a* will also minimize this gap 1015*a* which could potentially be a region where thrombus becomes trapped and later be sheared away since the small gap results in a small retaining force. Though the engaging members 1003 are generally capable of independent rotation, in scenarios where the engaging members are deployed in tortuous anatomy or are far oversized compared to the blood vessel, the engaging members can become stuck in a particular orientation limiting their ability to rotate. This rotation is generally advantageous since it allows the engaging elements to self-adjust to the condition of the vessel which maximizes the chances of clot contact and retention.

Figure 27:
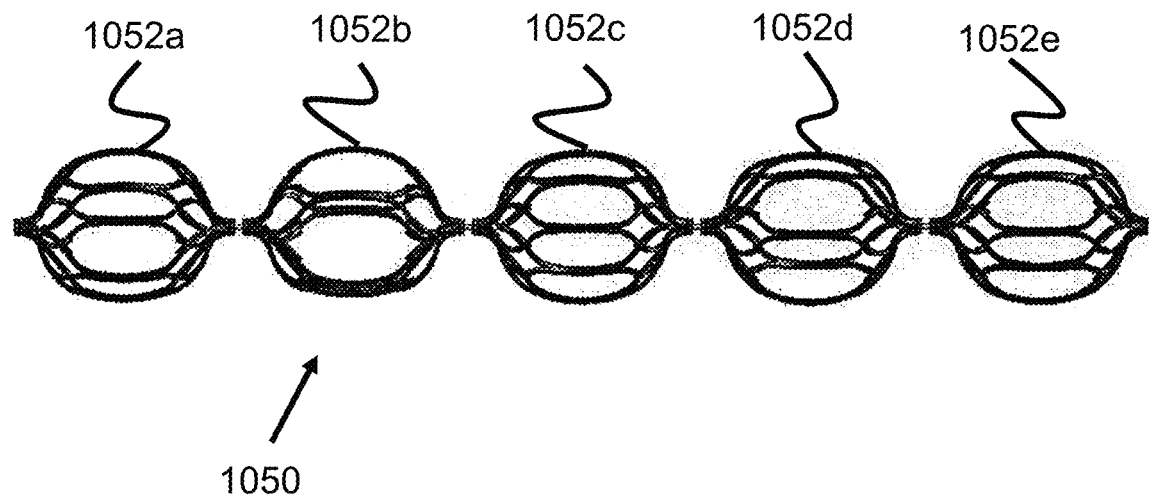
FIG. 27 illustrates an obstruction removal device with fixed engaging members.

FIG. 27 illustrates an embodiment of an obstruction removal device 1050 that addresses some of these issues. The device 1050 includes a series of engaging members 1052*a*-1052*e* (five are shown, but more engaging members or less engaging members could be used), where each engaging member is rotationally fixed in a particular orientation. Each engaging member has substantially the same strut pattern, however each engaging member is offset a certain number of degrees (i.e. rotated a particular number of degrees) from its neighboring engaging member 1052 and each engaging member is fixed and therefore incapable of independent rotation. As the entire obstruction removal device 1050 is pushed or pulled within a vessel, the fixed, offset arrangement of the engaging members 1052 ensure that all interior surfaces of the vessel are contacted by a strut of the engaging members 1052. In other words, if all of the engaging members 1052 where aligned in the same rotational orientation, linear gaps of the vessel's interior may not be contacted by the engaging members 1052. Hence, the rotational offset configuration helps mitigate this issue, particularly for larger clots that may span several engaging members.

Figure 28A:
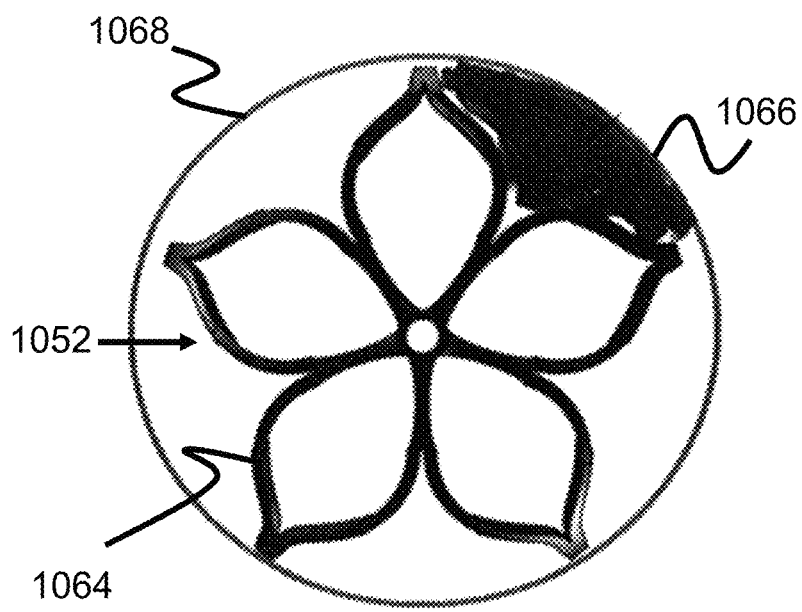
FIG. 28a illustrates a first embodiment of an obstruction removal device's interaction with thrombus against a vessel wall.

FIG. 28*a* shows one example involving a rare situation in which each engaging member is capable of independent rotation but some of the engaging members are stuck in the same or similar rotational orientation (for example, where the engaging members are deployed in a tortuous section of the vessel or are far oversized compared to the vessel and thereby stuck in one orientation). This figure offers a cross-sectional view from an end of one of the engaging members. Each end of each engaging member 1052 has a flowered petal bulb-type shape similar to the one shown in FIG. 1, the strut pairs merge into a lengthier strut which spans the majority of the engaging member 1052, and this lengthier strut then diverges into additional strut pairs at the other end of the engaging element and this flowered-type shape is repeated. Here, clot 406 is lodged against a particular section of the vessel wall 1068, but the struts 1064 of two or more neighboring engaging members are stuck in a similar position preventing the clot 1066 from being contacted by struts 1064. Conversely, in FIG. 28*b*, the fixed but offset strut orientation offers greater cross-sectional strut coverage around the periphery of the blood vessel 1068, which enhances the chances that the clot 406 is contacted.

Since the engaging members 10522*a*-10522*e* are fixed, the rotatable linking structure of FIG. 26, which includes gap 1015*a*, is not needed. In various embodiments, the engaging members can all be welded together or formed from one hypotube which is laser cut into the shape shown in FIG. 27. Either configuration will reduce or eliminate the gap between the engaging members which could potentially augment thrombus retention since this gap region potentially represents a region where thrombus could get temporarily stuck but later break free. The engaging members can also be placed over an open tubular lumen which spans all of the engaging members. This open tubular lumen can be used as a conduit for additional devices, including vessel filters placed downstream of the obstruction removal device to catch dislodged thrombus and/or guidewires used to aid in navigating the placement of the obstruction removal device. This design is also considerably simpler than the rotating engaging element embodiments since the paired linkage configurations are omitted.

In various examples, five engaging members are used and each engaging member is offset about 36 degrees from the next engaging member. Another example can utilize five engaging members offset about 18 degrees from the next engaging member. Other examples can utilize more or less engaging members with various degrees (e.g., from one degree to 359 degrees) of offset, the offset helps ensure a relatively broad cross section of the vessel will be exposed to at least one strut to aid in contacting the clot, thereby augmenting clot contact and clot retention. In other examples, some engaging members can be offset whereas other engaging members are not offset. In other examples, different offsets can be used between different engaging members (e.g. one pair offset by 20 degrees, another pair offset by 25 degrees).

Figure 28B:
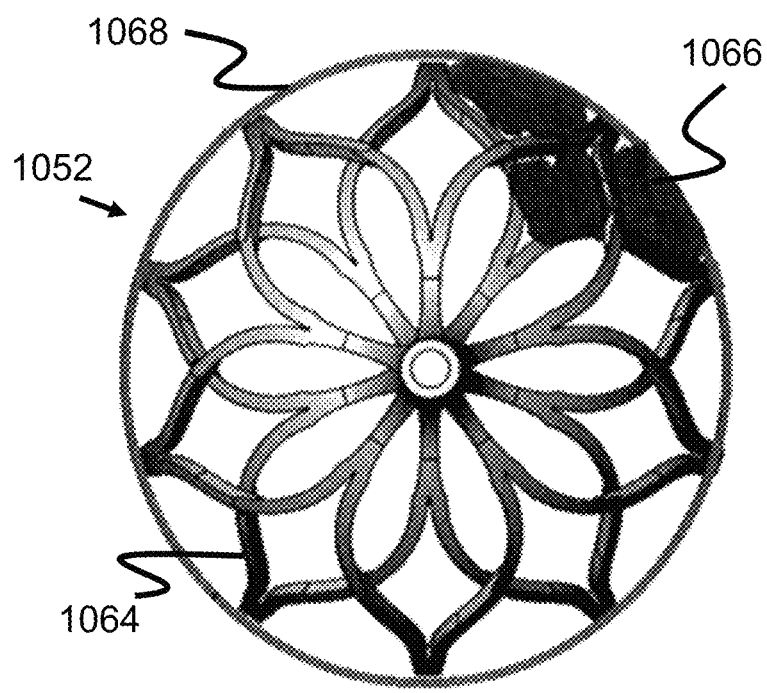
FIG. 28b illustrates a second embodiment of an obstruction removal device's interaction with thrombus against a vessel wall.

Various embodiments of the obstruction removal device, including various embodiments of the engaging elements comprising the obstruction removal device were presented in the specification herein. Please note, different versions of the obstruction removal device can utilize various engaging element shapes/configurations of different embodiments. By means of example, for the partially spanning strut engaging element configuration of FIG. 18, the engaging elements can utilize the twisted strut configuration of FIG. 20—alternatively some engaging elements can utilize a twisted strut configuration while others utilize the partially spanning strut configuration. Similarly, for the sliding embodiments of FIGS. 22-25, either the catch structures 906 or disruptor structures 908 can utilize partially spanning strut configurations and/or twisted strut configurations presented in various other embodiments. Similarly, in various embodiments (including the partially spanning strut configuration of FIG. 18, the twisted strut configuration of FIG. 20, or the sliding embodiments of FIGS. 22-25) some or all of the engaging members can be fixed but offset from other engaging members as shown in FIGS. 27-28*b*.

In an alternative embodiment, the device mentioned in the previous embodiments can be used to retrieve foreign objects, in addition to clots or other obstructions. Circumstances may arise where foreign objects, such as embolic coils normally used to fill an aneurysm, may break off or otherwise become detached within the vasculature. The device can be used to retrieve the foreign body utilizing a procedure similar to the procedure used during obstruction removal.

Figure 29:
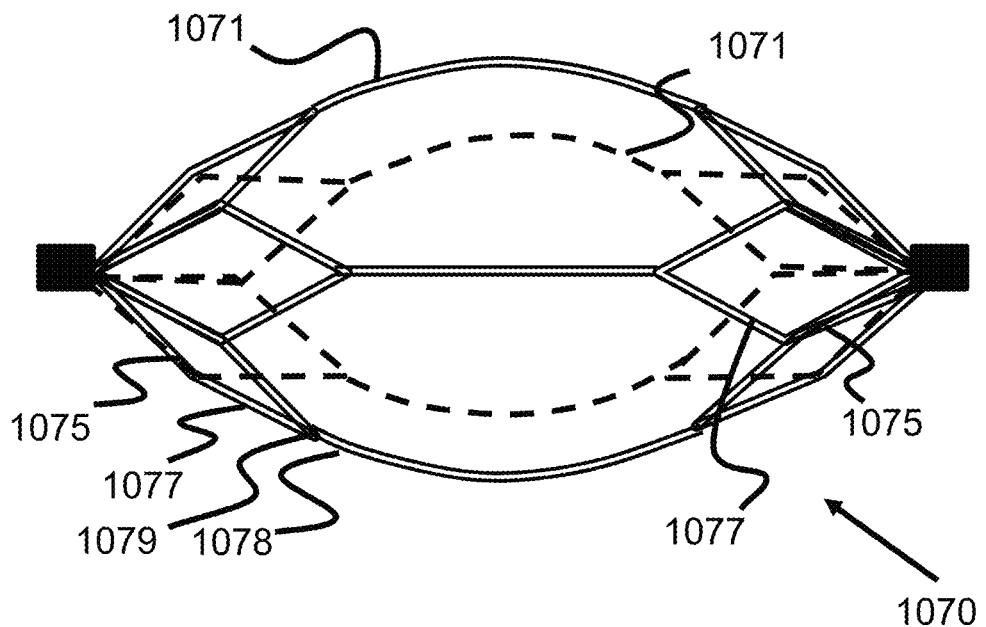
FIG. 29 illustrates an engaging member composed of drawn filled tube wires.

FIG. 29 illustrates and embodiment of an engaging member 1070 that, instead of being laser cut, is made from NiTi/Platinum drawn filled tube wires. These wires allow the engaging member 1070 to be fully radiopaque under fluoroscopy and therefore allow the physician to better place and control the device during a thrombectomy procedure. The engaging member 1070 is illustrated with primary struts 1075, secondary struts 1077 and lateral struts 1071, similar to previous embodiments; through any of the previous shapes/configurations can be used with these drawn filled tubes. Preferably, each of these struts are formed of individual drawn filled tube wires that are twisted together, for example at location 1079 to connect to adjacent struts. The proximal and distal ends of the engaging member 1070 can be laser welded to marker bands.

Figure 30:
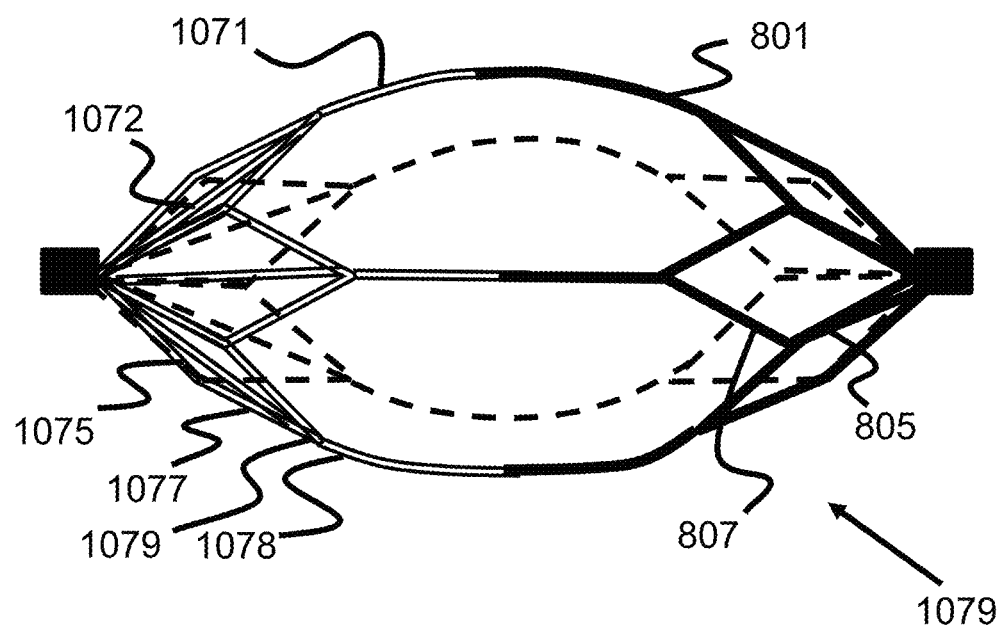
FIG. 30 illustrates an engaging member in which half of its structure is composed of drawn filled tube wires and its other half is composed of laser cut struts.

FIG. 30 illustrates an engaging member 1079 in which half of the struts 805, 807, and 801 are formed via laser cutting a metal sheet/tube, and the other half is formed of struts 1072, 1075, 1077, and 1078 of drawn filled tube wires. Preferably, the drawn filled tube wires are positioned on the distal end of the engaging member 1079 and the laser cut struts are positioned on the proximal end. The laser cut portion can provide a relatively higher radial expansion force while the drawn filled tube wires can allow for a greater number of wires to be used and therefore can increase the filtering capability of the device. Optionally, the drawn filled tube wires can be laser welded to the laser cut portion.

Figure 31:
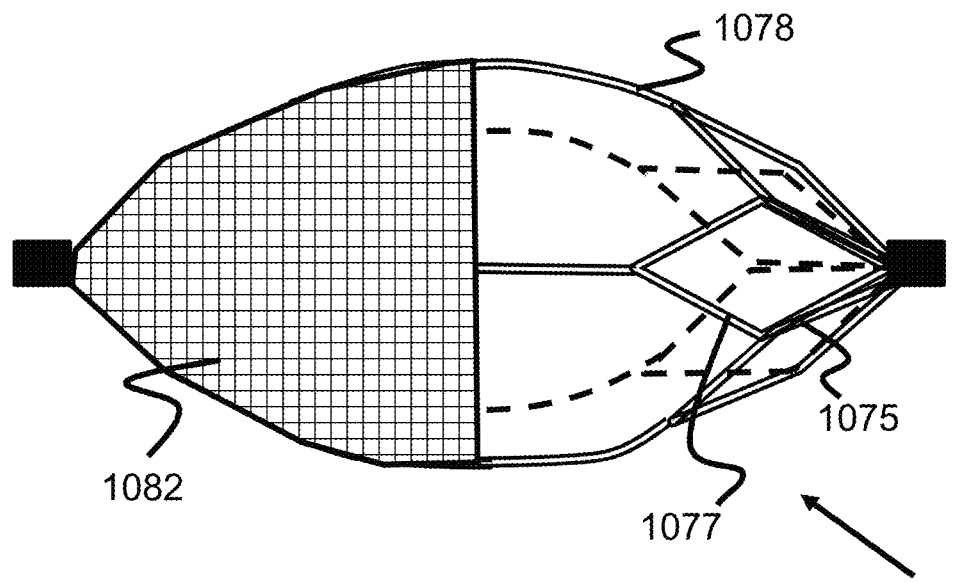
FIG. 31 illustrates an engaging member in which half of its structure is composed of drawn filled tube wires and its other half is composed of braided wires forming a mesh concave filter.

FIG. 31 illustrates another embodiment of an engaging member 1080 having a plurality of drawn filled tube wires 1075, 1077, 1078 on its proximal half in a configuration similar to those previously described, but also includes a distal half 1082 configured as a concave filter. The distal half 1082 is preferably formed of a plurality of drawn filled tube wires that are braided into the concave shape and welded to the larger drawn filled tube wires on the proximal half. In this respect, the distal half can act as a relatively fine filter and the proximal portion can provide the strength to radially expand the distal portion.

Figure 32:
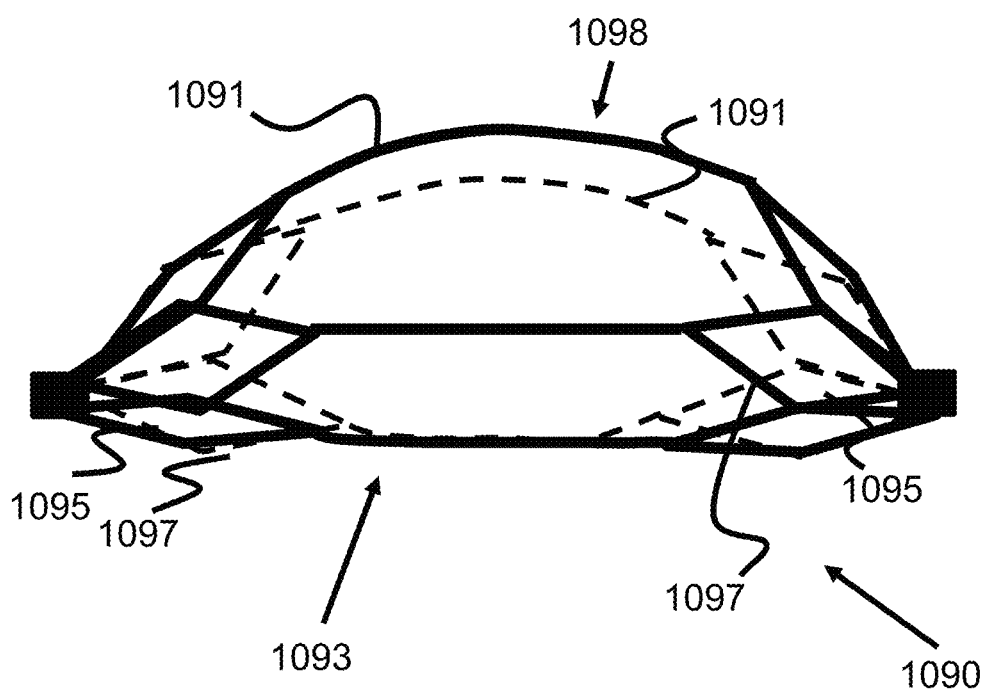
FIGS. 32 and 33 illustrate an engaging member that has a radially offset shape with a flat/straight side and a curved side.
Figure 33:
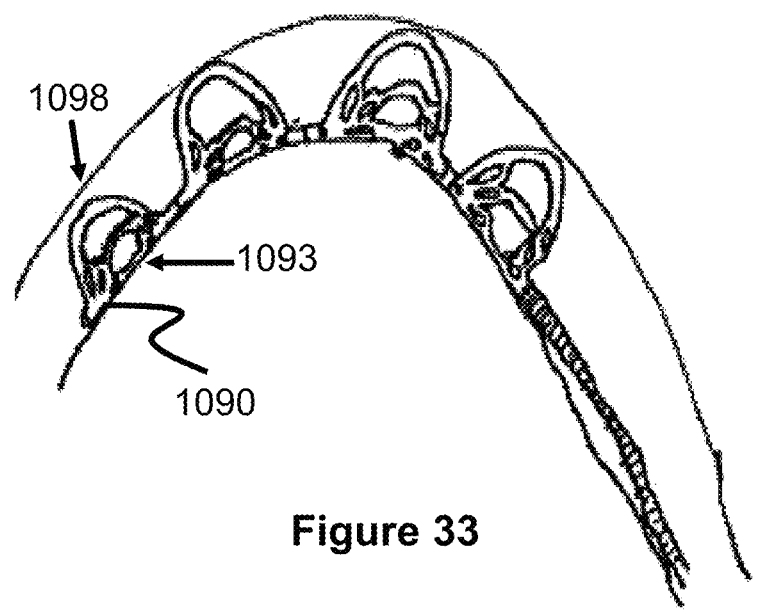

During a thrombectomy procedure, the previously described embodiments often much be moved around bends or curves within vessel, which can cause the engaging members to compress, as they seek out the shortest distance around the curves. This compression of the engaging members can cause the clot to dislodge and therefore be lost. The engaging member 1093 shown in FIGS. 32 and 33 address this issue by having a radially offset shape with a relatively straight/flat side 1093 and a relatively curved side 1098, all formed from struts 1095, 1097, and 1098. As seen in FIG. 33, as the offset engaging members 1093 are pulled around the curved vessel, their straight/flat side 1093 finds the shortest distance around the curve while the curved portion 1098 remains fully expanded.

Figure 34:
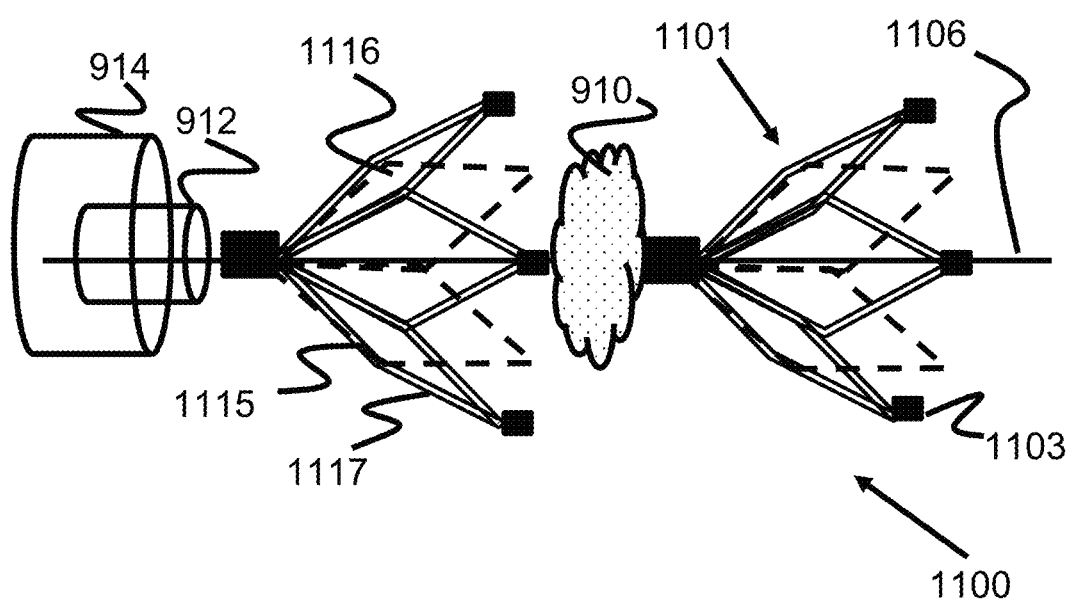
FIG. 34 illustrates a clot retrieval device having two flowering petal engaging members that open in a distal direction.

FIG. 34 illustrates another embodiment of a clot retrieval device 1100 having a proximal and distal "flowering petal" engaging members 1101 that re both connected to a delivery wire 1106. Similar to previously described embodiments, each engaging member 1101 are composed of a plurality of primary struts 1115 and secondary struts 1117, forming a plurality of connected diamond or loop shapes 1116 (e.g., 5 diamond shapes). The diamond shapes 1116 are included or are opened along a distal direction, forming a distally open cup or concave shape that can capture a clot 910. Each of the diamond shapes can include a radiopaque marker 1103 on its distal tip for use in determining their position during a procedure. Each engaging member 1101 can be fixed in place to the wire 1106, slideable on the wires 1106, or a combination of both (e.g., similar to the embodiment of FIG. 22). Preferably, the device 1100 is deployed during a procedure so that one engaging member 1101 is proximal to the clot 910 and the other engaging member 1101 is distal to the clot 910, trapping the clot 910. Alternately, the engaging members 1101 can open in the proximal direction or a combination of both (e.g., the proximal engaging member 1101 opens in the distal direction and the distal engaging member 1101 opens in the proximal direction). Additionally, more than two engaging members 1101 are also contemplated (e.g., 3, 4, 5, 6, 7, and 8).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An obstruction removal device comprising:
    a plurality of engaging members;
    a plurality of linkages;
    each engaging member connected to an adjacent engaging member by a linkage, each of the plurality of engaging members having a radially expanded configuration and a radially compressed configuration;

at least one proximal structure connected to one of the plurality of engaging members;
each engaging member composed of struts, where some struts span only part of a length of the engaging member;
wherein the struts that span only part of the length of the engaging member terminate in a projection which is thicker than the struts;
wherein the projection is a radiopaque marker, further includes adhesive to bind the struts to the radiopaque marker; and wherein the adhesive forms rounded shapes at both ends of said radiopaque marker.

2. The obstruction removal device of claim 1 wherein the projection is a radiopaque marker coil.

3. The obstruction removal device of claim 1 wherein the struts that span only part of the length of the engaging member begin at a common region, branch away from each other, and merge at or before the projection.

4. The obstruction removal device of claim 1 wherein the struts defining the engaging member are slanted relative to the wall of a blood vessel.

5. The obstruction removal device of claim 1 wherein at least one engaging member is fixed and at least one engaging member is sliding.

6. An obstruction removal device comprising:
a plurality of engaging members;
a plurality of linkages;
each engaging member connected to an adjacent engaging member by a linkage, each of the plurality of engaging members having a radially expanded configuration and a radially compressed configuration;
at least one proximal structure connected to one of the plurality of engaging members;
each engaging member composed of struts, where some struts span only part of a length of the engaging member;
wherein the struts that span only part of the length of the engaging member terminate in a projection which is thicker than the struts;
wherein some of the plurality of engaging members are fixed and radially offset from each other.

7. An obstruction removal system comprising:
a plurality of engaging members configured to be transported through a sheath, the plurality of engaging members each adopting a collapsed shape within the sheath and an expanded shape outside of the sheath;
a plurality of linkages, each linkage connecting two of the plurality of engaging members;
at least one proximal structure connected to one of the plurality of engaging members;
each of the plurality of engaging members composed of struts, where some struts span only part of a length of the engaging member;
wherein the struts that span only part of the length of the engaging member terminate in a projection which is thicker than the struts;
wherein some of the plurality of engaging members are fixed and radially offset from each other.

8. The obstruction removal device of claim 7 wherein the projection is a radiopaque marker.

9. The obstruction removal device of claim 7 wherein the projection is a radiopaque marker coil.

10. The obstruction removal device of claim 7 wherein the struts that span only part of the length of the engaging member begin at a common region, branch away from each other, and merge at or before the projection.

11. The obstruction removal device of claim 7 wherein the struts defining the engaging member are slanted relative to the wall of a blood vessel.

12. The obstruction removal system of claim 7 wherein the struts which span only part of the length of the engaging member span only a proximal portion of said engaging member.

13. The obstruction removal system of claim 7 wherein the struts which span only part of the length of the engaging member span only a distal portion of said engaging member.

14. The obstruction removal device of claim 7 wherein at least one engaging member is fixed and at least one engaging member is sliding.

\* \* \* \* \*